(12) United States Patent
Addison et al.

(10) Patent No.: US 8,289,501 B2
(45) Date of Patent: Oct. 16, 2012

(54) METHODS AND SYSTEMS FOR DISCRIMINATING BANDS IN SCALOGRAMS

(75) Inventors: Paul Stanley Addison, Edinburgh (GB);
James Watson, Dunfermline (GB);
David Clifton, Edinburgh (GB)

(73) Assignee: Nellcor Puritan Bennett Ireland, Mervue, Galway (IE)

( * ) Notice: Subject to any disclaimer, the term of this patent is extended or adjusted under 35 U.S.C. 154(b) by 0 days.

(21) Appl. No.: 13/292,524

(22) Filed: Nov. 9, 2011

(65) Prior Publication Data
US 2012/0123689 A1  May 17, 2012

Related U.S. Application Data

(63) Continuation of application No. 12/245,232, filed on Oct. 3, 2008, now Pat. No. 8,077,297.

(60) Provisional application No. 61/077,100, filed on Jun. 30, 2008, provisional application No. 61/077,130, filed on Jun. 30, 2008.

(51) Int. Cl.
*G01J 3/433* (2006.01)
(52) U.S. Cl. .......................................... 356/41; 600/323
(58) Field of Classification Search ............. 356/41, 356/39, 40, 42; 600/323, 324, 310, 508, 600/484, 529
See application file for complete search history.

(56) References Cited

U.S. PATENT DOCUMENTS

| | | | |
|---|---|---|---|
| 4,289,141 A | 9/1981 | Cormier |
| 5,285,783 A | 2/1994 | Secker |
| 5,291,884 A | 3/1994 | Heinemann et al. |
| 5,431,170 A | 7/1995 | Mathews |
| 5,439,483 A | 8/1995 | Duong-Van |
| 5,590,650 A | 1/1997 | Genova |
| 5,632,272 A | 5/1997 | Diab et al. |
| 5,778,881 A | 7/1998 | Sun et al. |
| 5,795,304 A | 8/1998 | Sun et al. |
| 5,797,840 A | 8/1998 | Akselrod et al. |
| 5,827,195 A | 10/1998 | Lander |
| 5,916,154 A | 6/1999 | Hobbs et al. |
| 5,967,995 A | 10/1999 | Shusterman et al. |
| 6,002,952 A | 12/1999 | Diab et al. |
| 6,011,985 A | 1/2000 | Athan et al. |
| 6,036,653 A | 3/2000 | Baba et al. |
| 6,094,592 A | 7/2000 | Yorkey et al. |
| 6,095,984 A | 8/2000 | Amano et al. |
| 6,117,075 A | 9/2000 | Barnea |

(Continued)

FOREIGN PATENT DOCUMENTS

JP  4-332536  11/1992
(Continued)

OTHER PUBLICATIONS

Addison, Paul S., The Illustrated Wavelet Transform Handbook, Taylor & Francis Group, 2002.

(Continued)

*Primary Examiner* — Layla Lauchman

(57) ABSTRACT

The present disclosure is directed towards embodiments of systems and methods for discriminating (e.g., masking out) scale bands that are determined to be not of interest from a scalogram derived from a continuous wavelet transform of a signal. Techniques for determining whether a scale band is not of interest include, for example, determining whether a scale band's amplitude is being modulated by one or more other bands in the scalogram. Another technique involves determining whether a scale band is located between two other bands and has energy less than that of its neighboring bands. Another technique involves determining whether a scale band is located at about half the scale of another, more dominant (i.e., higher energy) band.

20 Claims, 22 Drawing Sheets
(5 of 22 Drawing Sheet(s) Filed in Color)

U.S. PATENT DOCUMENTS

| | | |
|---|---|---|
| 6,129,675 A | 10/2000 | Jay |
| 6,135,966 A | 10/2000 | Ko |
| 6,151,518 A | 11/2000 | Hayashi |
| 6,163,715 A | 12/2000 | Larsen et al. |
| 6,171,257 B1 | 1/2001 | Weil et al. |
| 6,171,258 B1 | 1/2001 | Karakasoglu et al. |
| 6,181,958 B1 | 1/2001 | Steuer et al. |
| 6,208,951 B1 | 3/2001 | Kumar et al. |
| 6,217,523 B1 | 4/2001 | Amano et al. |
| 6,293,915 B1 | 9/2001 | Amano et al. |
| 6,325,761 B1 | 12/2001 | Jay |
| 6,352,502 B1 | 3/2002 | Chaiken et al. |
| 6,361,501 B1 | 3/2002 | Amano et al. |
| 6,393,311 B1 | 5/2002 | Edgar, Jr. et al. |
| 6,415,166 B1 | 7/2002 | Van Hoy et al. |
| 6,453,184 B1 | 9/2002 | Hyogo et al. |
| 6,510,331 B1 | 1/2003 | Williams et al. |
| 6,516,209 B2 | 2/2003 | Cheng et al. |
| 6,526,301 B2 | 2/2003 | Larsen et al. |
| 6,553,242 B1 | 4/2003 | Sarussi |
| 6,561,986 B2 | 5/2003 | Baura et al. |
| 6,608,934 B2 | 8/2003 | Scheirer et al. |
| 6,654,622 B1 | 11/2003 | Eberhard et al. |
| 6,654,623 B1 | 11/2003 | Kastle |
| 6,709,402 B2 | 3/2004 | Dekker |
| 6,748,252 B2 | 6/2004 | Lynn et al. |
| 6,760,610 B2 | 7/2004 | Tschupp et al. |
| 6,773,397 B2 | 8/2004 | Kelly |
| 6,810,277 B2 | 10/2004 | Edgar, Jr. et al. |
| 6,909,912 B2 | 6/2005 | Melker |
| 6,931,269 B2 | 8/2005 | Terry |
| 6,985,762 B2 | 1/2006 | Brashears et al. |
| 7,001,337 B2 | 2/2006 | Dekker |
| 7,020,507 B2 | 3/2006 | Scharf et al. |
| 7,035,679 B2 | 4/2006 | Addison et al. |
| 7,043,293 B1 | 5/2006 | Baura |
| 7,054,453 B2 | 5/2006 | Causevic et al. |
| 7,054,454 B2 | 5/2006 | Causevic et al. |
| 7,079,888 B2 | 7/2006 | Oung et al. |
| 7,171,269 B1 | 1/2007 | Addison et al. |
| 7,173,525 B2 | 2/2007 | Albert |
| 7,203,267 B2 | 4/2007 | De Man et al. |
| 7,209,775 B2 | 4/2007 | Bae et al. |
| 7,222,054 B2 | 5/2007 | Geva |
| 7,225,013 B2 | 5/2007 | Geva et al. |
| 7,254,432 B2 | 8/2007 | Fine |
| 7,254,500 B2 | 8/2007 | Makeig et al. |
| 7,289,835 B2 | 10/2007 | Mansfield et al. |
| 7,309,314 B2 | 12/2007 | Grant et al. |
| 7,341,560 B2 | 3/2008 | Henderson et al. |
| 7,349,727 B2 | 3/2008 | Obata et al. |
| 7,353,054 B2 | 4/2008 | Kawasaki et al. |
| 7,387,607 B2 | 6/2008 | Holt et al. |
| 7,398,115 B2 | 7/2008 | Lynn |
| 7,431,696 B1 | 10/2008 | Brady et al. |
| 7,515,949 B2 | 4/2009 | Norris |
| 7,519,488 B2 | 4/2009 | Fu et al. |
| 7,523,011 B2 | 4/2009 | Akiyama et al. |
| 7,751,873 B2 | 7/2010 | de Voir |
| 2001/0051767 A1 | 12/2001 | Williams et al. |
| 2003/0163057 A1 | 8/2003 | Flick et al. |
| 2005/0043616 A1 | 2/2005 | Chinchoy |
| 2005/0070774 A1 | 3/2005 | Addison et al. |
| 2005/0085735 A1 | 4/2005 | Baker et al. |
| 2005/0119708 A1 | 6/2005 | Haefner |
| 2005/0192493 A1 | 9/2005 | Wuori |
| 2005/0197552 A1 | 9/2005 | Baker |
| 2005/0267346 A1 | 12/2005 | Faber et al. |
| 2006/0058595 A1 | 3/2006 | Herrmann |
| 2006/0092029 A1 | 5/2006 | Browne et al. |
| 2006/0155206 A1 | 7/2006 | Lynn |
| 2006/0189880 A1 | 8/2006 | Lynn et al. |
| 2006/0209631 A1 | 9/2006 | Melese et al. |
| 2006/0211930 A1 | 9/2006 | Scharf et al. |
| 2006/0229519 A1 | 10/2006 | Fujiwara et al. |
| 2006/0258921 A1 | 11/2006 | Addison et al. |
| 2006/0265022 A1 | 11/2006 | John et al. |
| 2006/0276697 A1 | 12/2006 | Demuth et al. |
| 2007/0021673 A1 | 1/2007 | Arbel et al. |
| 2007/0027368 A1 | 2/2007 | Collins et al. |
| 2007/0073120 A1 | 3/2007 | Li et al. |
| 2007/0073124 A1 | 3/2007 | Li et al. |
| 2007/0083097 A1 | 4/2007 | Fujiwara et al. |
| 2007/0118028 A1 | 5/2007 | Kitajima et al. |
| 2007/0129647 A1 | 6/2007 | Lynn |
| 2007/0142719 A1 | 6/2007 | Kawasaki et al. |
| 2007/0167694 A1 | 7/2007 | Causevic et al. |
| 2007/0167851 A1 | 7/2007 | Vitali et al. |
| 2007/0213621 A1 | 9/2007 | Reisfeld et al. |
| 2007/0213622 A1 | 9/2007 | Reisfeld |
| 2007/0219439 A1 | 9/2007 | Vilser et al. |
| 2007/0282212 A1 | 12/2007 | Sierra et al. |
| 2007/0299323 A1 | 12/2007 | Arns et al. |
| 2008/0045832 A1 | 2/2008 | McGrath |
| 2008/0076992 A1 | 3/2008 | Hete et al. |
| 2008/0077026 A1 | 3/2008 | Banet et al. |
| 2008/0082018 A1 | 4/2008 | Sackner et al. |
| 2008/0146901 A1 | 6/2008 | Katura et al. |
| 2008/0188733 A1 | 8/2008 | Al-Ali et al. |
| 2008/0200775 A1 | 8/2008 | Lynn |
| 2008/0214903 A1 | 9/2008 | Orbach |
| 2008/0243021 A1 | 10/2008 | Causevic et al. |
| 2008/0262326 A1 | 10/2008 | Hete et al. |
| 2008/0296514 A1 | 12/2008 | Metzger et al. |

FOREIGN PATENT DOCUMENTS

| | | |
|---|---|---|
| JP | 2004-135854 | 5/2004 |
| JP | 2004-194908 | 7/2004 |
| JP | 2004-261364 | 9/2004 |
| JP | 3825459 | 4/2005 |
| JP | 2006-158974 | 6/2006 |
| JP | 2007-267761 | 10/2007 |
| JP | 2007-319247 | 12/2007 |
| JP | 2008-110108 | 5/2008 |
| JP | 2008-161657 | 7/2008 |
| WO | WO 91/11137 | 8/1991 |
| WO | WO 01/025802 | 4/2001 |
| WO | WO 01/062152 | 8/2001 |
| WO | WO 03/000125 | 1/2003 |
| WO | WO 03/039326 | 5/2003 |
| WO | WO 03/055395 | 7/2003 |
| WO | WO 2004/075746 | 9/2004 |
| WO | WO 2004/105601 | 12/2004 |
| WO | WO 2005/009221 | 2/2005 |
| WO | WO 2005/064314 | 7/2005 |
| WO | WO 2005/096170 | 10/2005 |
| WO | WO 2006/085120 | 8/2006 |
| WO | WO 2006/100685 | 9/2006 |
| WO | WO 2007/048989 | 5/2007 |

OTHER PUBLICATIONS

Addison, Paul, "The Little Wave with the Big Future," Physics World, Mar. 2004, pp. 35-39.

Clifton, David, Douglas, J. Graham, Addison, Paul S., Watson, James N., "Measurement of Respiratory Rate from the Photoplethysmogram in Chest Clinic Patients," Journal of Clinical Monitoring and Computing, 2006.

Dirk Hoyer et al., A New Approach to Uncover Dynamic Phase Coordination and Synchronization, IEEE Transactions of Biomedical Engineering, IEEE Service Center, Piscataway, NJ, US, vol. 47, No. 1, Jan. 1, 2000, XP011006818, ISSN: 0018-9294, Section II, B and C, Section III.B.

Holfeld, Rg and Rajagopalan, C. and Neff, GW: "Wavelet signal processing of physiologic waveforms" Wavelet Technologies Inc. White Paper, 2004, pp. 1-24, XP002612138, Secion III.3 Figure 8.

Leonard, Paul A., Douglas, J. Graham, Grubb, Neil R., Clifton, David, Addison, Paul S., Watson, James N., "A Fully Automated Algorithm for the Determination of Respiratory Rate From the Photoplethysmogram," Journal of Clinical Monitoring and Computing, 2006.

Leonard, Paul A., Clifton, David, Addison, Paul S., Watson, James N., Beattie, Tom "An Automated Algorithm for Determining Respiratory Rate by Photoplethysmogram in Children," Acta Paediatricia, 2006; 95: 1124-1128.

Legarreta, I. Romero, Addison, P. S., Reed, M. J., Grubb, N. Clegg, G. R., Robertson, C. E., Watson, J. N., "Continuous Wavelet Transform Modulus Maxima Analysis of the Electrocardiogram: Beat Characterisation and Beat-to-Beat Measurement," International Journal of Wavelets, Multiresolution and Information Processing, vol. 3, No. 1, 2004, pp. 1-24.

"One-Dimensional Continuous Wavelet Analysis", Matlab R2020b MathWorks Documentation—Wavelet Toolbox, Sep. 2010, XP002612139, retrieved from the Internet: URL:http://www.mathworks.com/help/toolbox/wavelet/gs/f4-1000108.html [retrieved on Nov. 2010] the whole document.

PCT Invitation to Pay Additional Fees and, Where Applicable, Protest Fee, Date of Mailing Dec. 14, 2010, Applicant's reference MK/P16361WO PE95/905WO, International application No. PCT/IB2009/006181, International Filing Date Jun. 29, 2009.

Ponomarkenko VI et al.: Deriving main rhythms of the human cardiovascular system from the heartbeat time series and detecting their synchronization: Chaos, Solitons and Fractals, Pergamon, Oxford, GB, vol. 23, No. 4, Feb. 1, 2005, pp. 1429-1438, XP025298901. ISSN: 0960-0779 [retrieved on Feb. 1, 2005] Section 2 and 3.

Tse PW et al.: "Machine fault diagnosis through an effective exact wavelet analysis", Journal of Sound & Vibration, London, GB, vol. 277, No. 4-5, Nov. 5, 2004, pp. 1005-1024, XP004562805, ISSN: 0022-460X, DOI: DOI: 10.1016/J.JSV.2003.09.031 Abstract, Section 2.

Yamada, Michio, "Wavelet Analysis and Its Application," Journal of the Institute of Electronics, Information and Communication Engineers, vol. 76, No. 5, May 1993, pp. 518-528.

METHODS AND SYSTEMS FOR DISCRIMINATING BANDS IN SCALOGRAMS

CROSS-REFERENCE TO RELATED APPLICATIONS

This application is a continuation application of U.S. patent application Ser. No. 12/245,232, filed Oct. 3, 2008 (now allowed), and claims the benefit of U.S. Provisional Application No. 61/077,100, entitled "Methods and Systems for Discriminating Bands in Scalograms," filed Jun. 30, 2008 (now expired), and U.S. Provisional Application No. 61/077,130, entitled "Systems and Methods of Signal Processing," filed Jun. 30, 2008 (now expired), which are hereby incorporated by reference herein in their entireties.

SUMMARY

The present disclosure relates to signal processing and, more particularly, the present disclosure relates to using continuous wavelet transforms for processing, for example, a photoplethysmograph (PPG) signal.

In connection with deriving useful information (e.g., clinical information) from one or more bands of interest from a scalogram, an analysis may be performed to identify those bands that are likely to contain the information sought as well as to identify those bands that are likely due to noise or any other phenomena. The present disclosure, provides techniques for discriminating bands that are not of interest prior to performing further analysis of the scalogram.

For purposes of clarity, and not by way of limitation, some embodiments disclosed herein may include a process for identifying and discriminating bands of a scalogram generated at least in part from a PPG signal transformed by a continuous wavelet transform. In the context of a PPG signal obtained from a patient, taking the wavelet transform of the PPG signal and generating a scalogram from the transformed signal may yield clinically relevant information about, among other things, the pulse rate and breathing rate of the patient. In order to garner information about pulse rate and breathing rate, however, the pulse band and the breathing band of the scalogram associated with these rates may need to be identified from among a plurality of other bands on the scalogram that may not be of interest and that may be discriminated using any of the techniques disclosed herein.

In an embodiment, a band that may not be of interest may be identified by determining whether the band is being modulated by another band. For example, a band of interest (e.g., a pulse band or a breathing band) may cause another band (e.g., the band that is not of interest) to appear on the scalogram and be modulated at the scale of the band of interest. The detection of the modulation may be performed in any suitable way, including, for example, by using a mod-max discriminator or by taking an Fast Fourier Transform or any other suitable transform (e.g., a secondary wavelet transform) of the amplitude modulation of the ridge or band that is not of interest and comparing the transformed result to the scale of the other ridge, ridges, band or bands that are of interest. Alternatively, the modulation may be detected by filtering the original signal at the scale(s) that may be associated with the band(s) of interest.

In an embodiment, a band that may not be of clinical interest also may be identified by determining whether that band is coupled to a band that is of clinical interest. In another embodiment, a band that is not of interest may be identified by examining the scalogram at scales that may be approximately half of the value of the scales associated with one or more bands of interest. After a band has been identified as being not of interest, whether by the techniques discussed herein or by any other suitable technique, that band may be discriminated prior to any farther analysis of the scalogram.

In an embodiment, a method is provided. The method may include receiving a signal, generating a scalogram based at least in part on a continuous wavelet transform of the signal, determining whether at least one band of scales from the scalogram is not of interest, and discriminating the at least one band of scales if it is determined to be not of interest.

In an embodiment, a system for discriminating at least one band of scales is provided. The system may include a processor. The processor may be capable of receiving an input signal, generating a scalogram based at least in part on a continuous wavelet transform of the input signal, determining whether at least one band of scales from the scalogram is not of interest, and discriminating the at least one band of scales if it is determined to be not of interest.

In an embodiment, a computer-readable medium having computer program instructions stored thereon is provided. The computer program instructions, if executed by a machine, may be capable of generating a scalogram based at least in part on a continuous wavelet transform of an input signal, determining whether at least one band of scales from the scalogram is not of interest to a pulse rate or a breathing rate of the patient, and discriminating the at least one band of scales if it is determined to be not of interest.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other features of the present disclosure, its nature and various advantages will be more apparent upon consideration of the following detailed description, taken in conjunction with the accompanying drawings in which.

DETAILED DESCRIPTION

Figure 1:
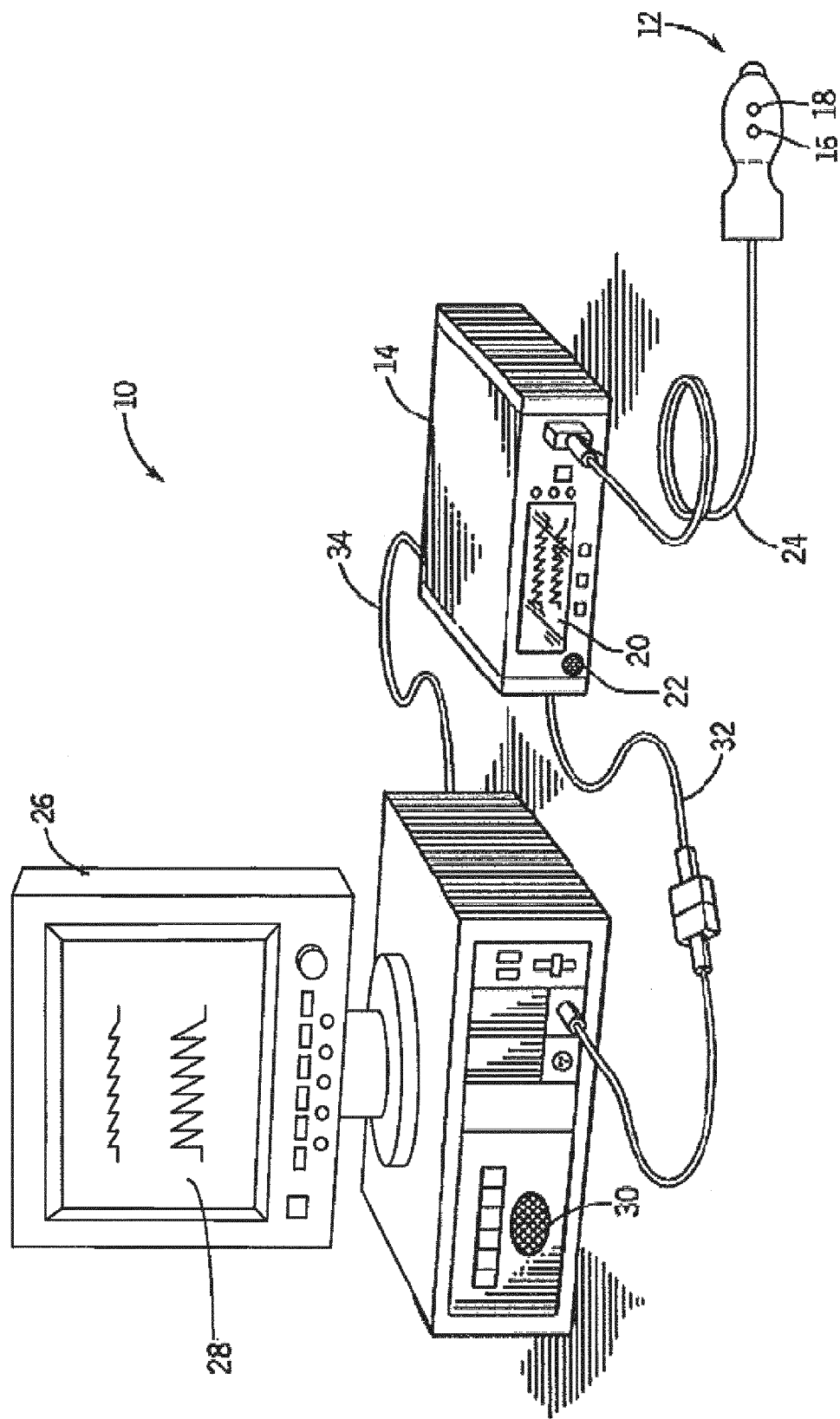
FIG. 1 shows an illustrative pulse oximetry system in accordance with an embodiment.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a sealed version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based on Lambert-Beer's law. The following notation will be used herein:

$$I(\lambda,t)=I_0(\lambda)\exp(-(s\beta_o(\lambda)+(1-s)\beta_r(\lambda))l(t)) \quad (1)$$

where:
$\lambda$=wavelength;
t=time;
I=intensity of light detected;
$I_0$=intensity of light transmitted;
s=oxygen saturation;
$\beta_o$, $\beta_r$=empirically derived absorption coefficients; and
l(t)=a combination of concentration and path length from emitter to detector as a function of time.

The traditional approach measures light absorption at two wavelengths (e.g., red and infrared (IR)), and then calculates saturation by solving for the "ratio of ratios" as follows.

1. First, the natural logarithm of (1) is taken ("log" will be used to represent the natural logarithm) for IR and Red $$\log I = \log I_0 - (s\beta_o + (1-s)\beta_r)l \quad (2)$$

2. (2) is then differentiated with respect to time $$\frac{d\log I}{dt} = -(s\beta_o + (1-s)\beta_r)\frac{dl}{dt} \quad (3)$$

3. Red (3) is divided by IR (3)

$$\frac{\frac{d\log I(\lambda_R)}{dt}}{\frac{d\log I(\lambda_{IR})}{dt}} = \frac{s\beta_o(\lambda_R) + (1-s)\beta_r(\lambda_R)}{s\beta_o(\lambda_{IR}) + (1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR}) - \beta_r(\lambda_{IR})) - \frac{d\log I(\lambda_{IR})}{dt}(\beta_o(\lambda_R) - \beta_r(\lambda_R))}$$

Note in discrete time $$\frac{d\log I(\lambda, t)}{dt} \simeq \log I(\lambda, t_2) - \log I(\lambda, t_1)$$

Using log A−log B=log A/B, $$\frac{d\log I(\lambda, t)}{dt} \simeq \log\left(\frac{I(t_2, \lambda)}{I(t_1, \lambda)}\right)$$

So, (4) can be rewritten as $$\frac{\frac{d\log I(\lambda_R)}{dt}}{\frac{d\log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R \quad (5)$$

where R represents the "ratio of ratios." Solving (4) for s using (5) gives $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}.$$

From (5), R can be calculated using two points (e.g., PPG maximum and minimum), or a family of points. One method using a family of points uses a modified version of (5), Using the relationship $$\frac{d\log I}{dt} = \frac{\frac{dI}{dt}}{I} \quad (6)$$

now (5) becomes $$\frac{\frac{d\log I(\lambda_R)}{dt}}{\frac{d\log I(\lambda_{IR})}{dt}} \simeq \frac{\frac{I(t_2, \lambda_R) - I(t_1, \lambda_R)}{I(t_1, \lambda_R)}}{\frac{I(t_2, \lambda_{IR}) - I(t_1, \lambda_{IR})}{I(t_1, \lambda_{IR})}} = \quad (7)$$

$$\frac{[I(t_2, \lambda_R) - I(t_1, \lambda_R)]I(t_1, \lambda_{IR})}{[I(t_2, \lambda_{IR}) - I(t_1, \lambda_{IR})]I(t_1, \lambda_R)} = R$$

which defines a cluster of points whose slope of y versus x will give R where $x(t) = [I(t_2, \lambda_{IR}) - I(t_1, \lambda_{IR})]I(t_1, \lambda_R)$ $y(t) = [I(t_2, \lambda_R) - I(t_1, \lambda_R)]I(t_1, \lambda_{IR})$ $y(t) = Rx(t) \quad (8)$ FIG. 1 is a perspective view of an embodiment of a pulse oximetry system 10. System 10 may include a sensor 12 and a pulse oximetry monitor 14. Sensor 12 may include an emitter 16 for emitting light at two or more wavelengths into a patient's tissue. A detector 18 may also be provided in sensor 12 for detecting the light originally from emitter 16 that emanates from the patient's tissue after passing through the tissue.

According to another embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and am sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry data from a patient's forehead.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data received from sensor 12 relating to light emission and detection. In an alternative embodiment, the calculations may be performed on the monitoring device itself and the result of the oximetry reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, pulse oximetry system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multiparameter patient monitor 26 may be configured to display an estimate of a patient's blood oxygen saturation generated by pulse oximetry monitor 14 (referred to as an "SpO$_2$" measurement), pulse rate information from monitor 14 and blood pressure from a blood pressure monitor (not shown) on display 28.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Figure 2:
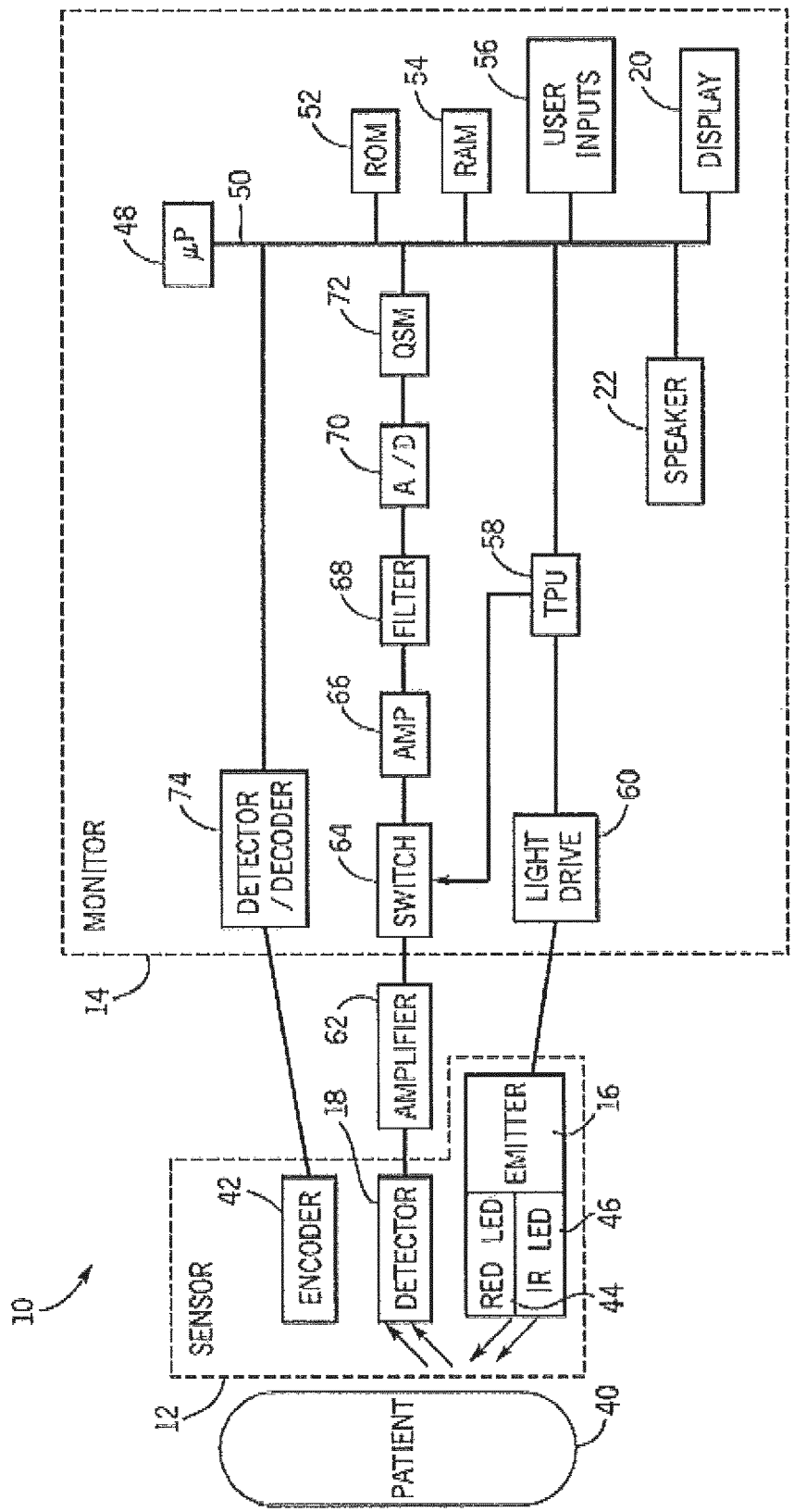
FIG. 2 is a block diagram of the illustrative pulse oximetry system of FIG. 1 coupled to a patient in accordance with an embodiment.

FIG. 2 is a block diagram of a pulse oximetry system, such as pulse oximetry system 10 of FIG. 1, which may be coupled to a patient 40 in accordance with an embodiment. Certain illustrative components of sensor 12 and monitor 14 are illustrated in FIG. 2. Sensor 12 may include emitter 16, detector 18, and encoder 42, In the embodiment shown, emitter 16 may be configured to emit at least two wavelengths of light (e.g., RED and IR) into a patient's tissue 40. Hence, emitter 16 may include a RED light emitting light source such as RED light emitting diode (LED) 44 and an IR light emitting light source such as IR LED 46 for emitting light into the patient's tissue 40 at the wavelengths used to calculate the patient's physiological parameters, In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the RED and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The Light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the RED and IR wavelengths in the patient's tissue 40.

In an embodiment, encoder 42 may contain information about sensor 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelengths of light emitted by emitter 16 on each sensor of the sensor array, and/or the patient's characteristics. In another embodiment, encoder 42 may include as memory on which one or more of the following information may be stored for communication to monitor 14: the type of the sensor 12; the wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as $SpO_2$ and pulse rate, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the oximeter probe is attached.

Noise (e.g., from patient movement) can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site. Processing pulse oximetry (i.e., PPG) signals may involve operations that reduce the amount of noise present in the signals or otherwise identify noise components in order to prevent them from affecting measurements of physiological parameters derived from the PPG signals.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In one embodiment, a PPG signal may be transformed using a continuous wavelet transform. Information derived from the transform of the PPG signal (i.e., in wavelet space) may be used to provide measurements of one or more physiological parameters.

The continuous wavelet transform of a signal x(t) in accordance with the present disclosure may be defined as $$T(a, b) = \frac{1}{\sqrt{a}} \int_{-\infty}^{+\infty} x(t)\psi^*\left(\frac{t-b}{a}\right) dt \qquad (9)$$

where $\psi^*(t)$ is the complex conjugate of the wavelet function $\psi(t)$, a is the dilation parameter of the wavelet and b is the location parameter of the wavelet. The transform given by equation (9) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b) = |T(a,b)|^2 \qquad (10)$$

where '||' is the modulus operator. The scalogram may be rescaled for useful purposes. One common rescaling is defined as $$S_R(a, b) = \frac{|T(a, b)|^2}{a} \qquad (11)$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane are labeled a "maxima ridge"

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by $\sqrt{a}$.

In the discussion of the technology which follows herein, the "scalogram" may be taken to include all suitable forms of resealing including, but not limited to, the original unsealed wavelet representation, linear resealing, any power of the modulus of the wavelet transform, or any other suitable resealing. In addition, for purposes of clarity and conciseness, the term "scalogram" shall be taken to mean the wavelet transform, $T(a,b)$ itself, or any part thereof. For example, the real part of the wavelet transform, the imaginary pad of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The Characteristic frequency associated with a wavelet of arbitrary a scale is given by $$f = \frac{f_c}{a} \quad (12)$$

where $f_c$, the characteristic frequency of the mother wavelet (i.e., at $a=1$), becomes a scaling constant and $f$ is the representative or characteristic frequency for the wavelet at arbitrary scale $a$.

Any suitable wavelet function may be used in connection with the present disclosure. One of the most commonly used complex wavelets, the Morlet wavelet, is defined as:

$$\psi(t) = \pi^{-1/4}(e^{i2\pi f_0 t} - e^{-(2\pi f_0)^2/2})e^{-t^2/2} \quad (13)$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as $$\psi(t) = \frac{1}{\pi^{1/4}} e^{i2\pi f_0 t} e^{-t^2/2} \quad (14)$$

This wavelet is a complex wave within a scaled Gaussian envelope. While both definitions of the Morlet wavelet are included herein, the function of equation (14) is not strictly a wavelet as it has a non-zero mean (i.e., the zero frequency term of its corresponding energy spectrum is non-zero). However, it will be recognized by those skilled in the art that equation (14) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of PPG signals may be used to provide clinically useful information within a medical device.

Figure 3B:
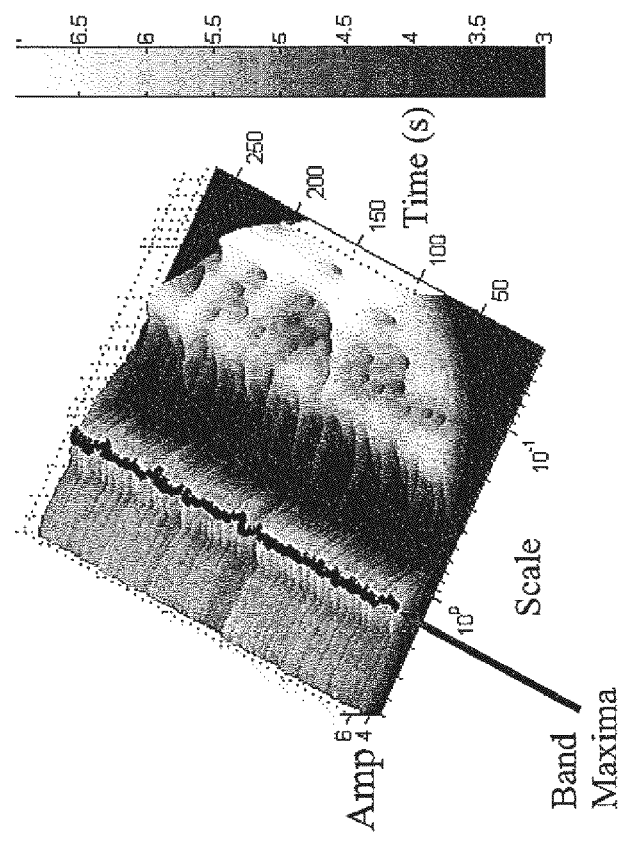
FIGS. 3(a) and 3(b) show illustrative views of a scalogram derived from a PPG signal in accordance with an embodiment.
Figure 3A:
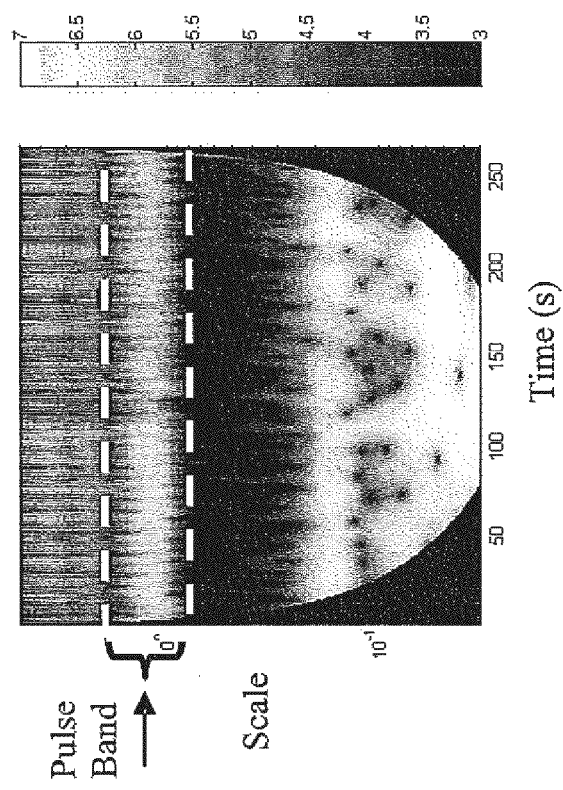

Pertinent repeating features in a signal give rise to a time-scale band in wavelet space or a resealed wavelet space. For example, the pulse component of a PPG signal produces a dominant band in wavelet space at or around the pulse frequency. FIGS. 3(a) and (b) show two views of an illustrative scalogram derived from a PPG signal, according to an embodiment. The figures show an example of the band caused by the pulse component in such a signal. The pulse band is located between the dashed lines in the plot of FIG. 3(a). The band is formed from a series of dominant coalescing features across the scalogram. This can be clearly seen as a raised band across the transform surface in FIG. 3(b) located within the region of scales indicated by the arrow in the plot (corresponding to 60 beats per minute). The maxima of this band with respect to scale is the ridge. The locus of the ridge is shown as a black curve on top of the band in FIG. 3(b). By employing a suitable resealing of the scalogram, such as that given in equation (11), the ridges found in wavelet space may be related to the instantaneous frequency of the signal. In this way, the pulse rate may be obtained from the PPG signal. Instead of resealing the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 3C:
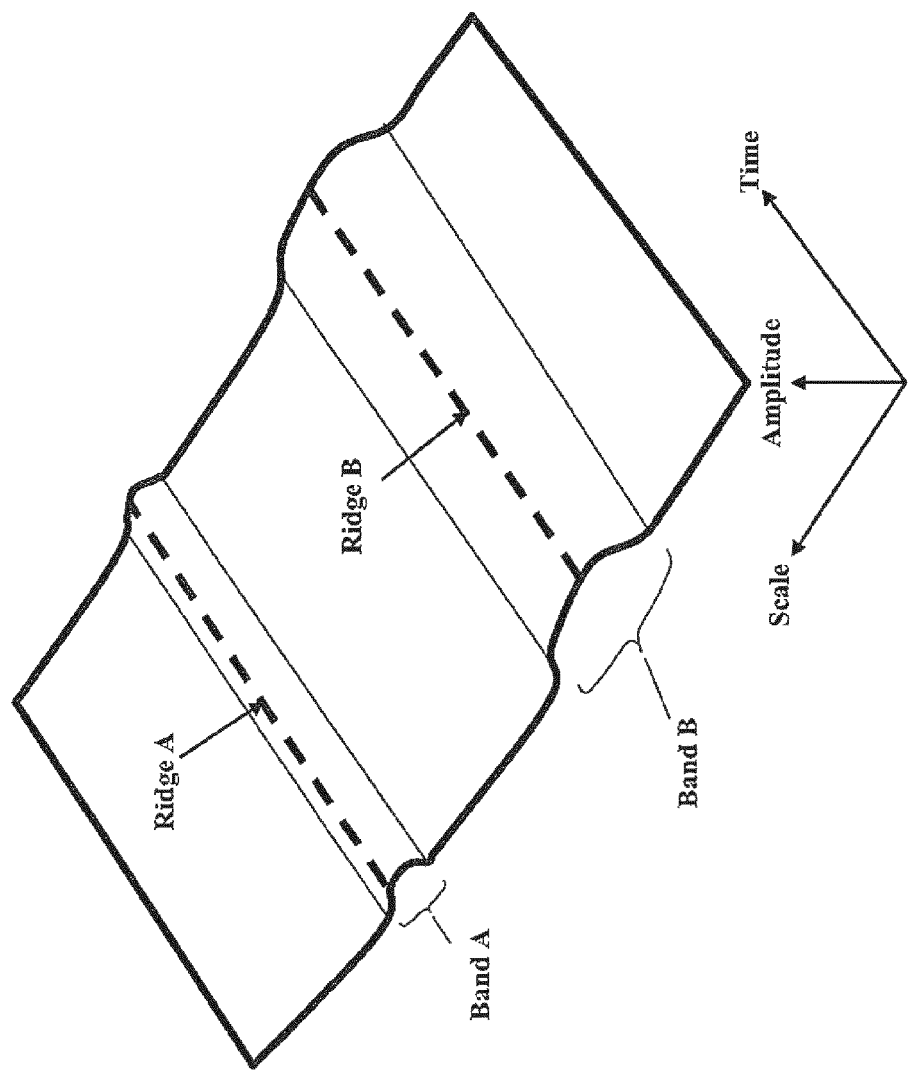
FIG. 3(c) shows an illustrative scalogram derived from a signal containing two pertinent components in accordance with an embodiment.
Figure 3D:
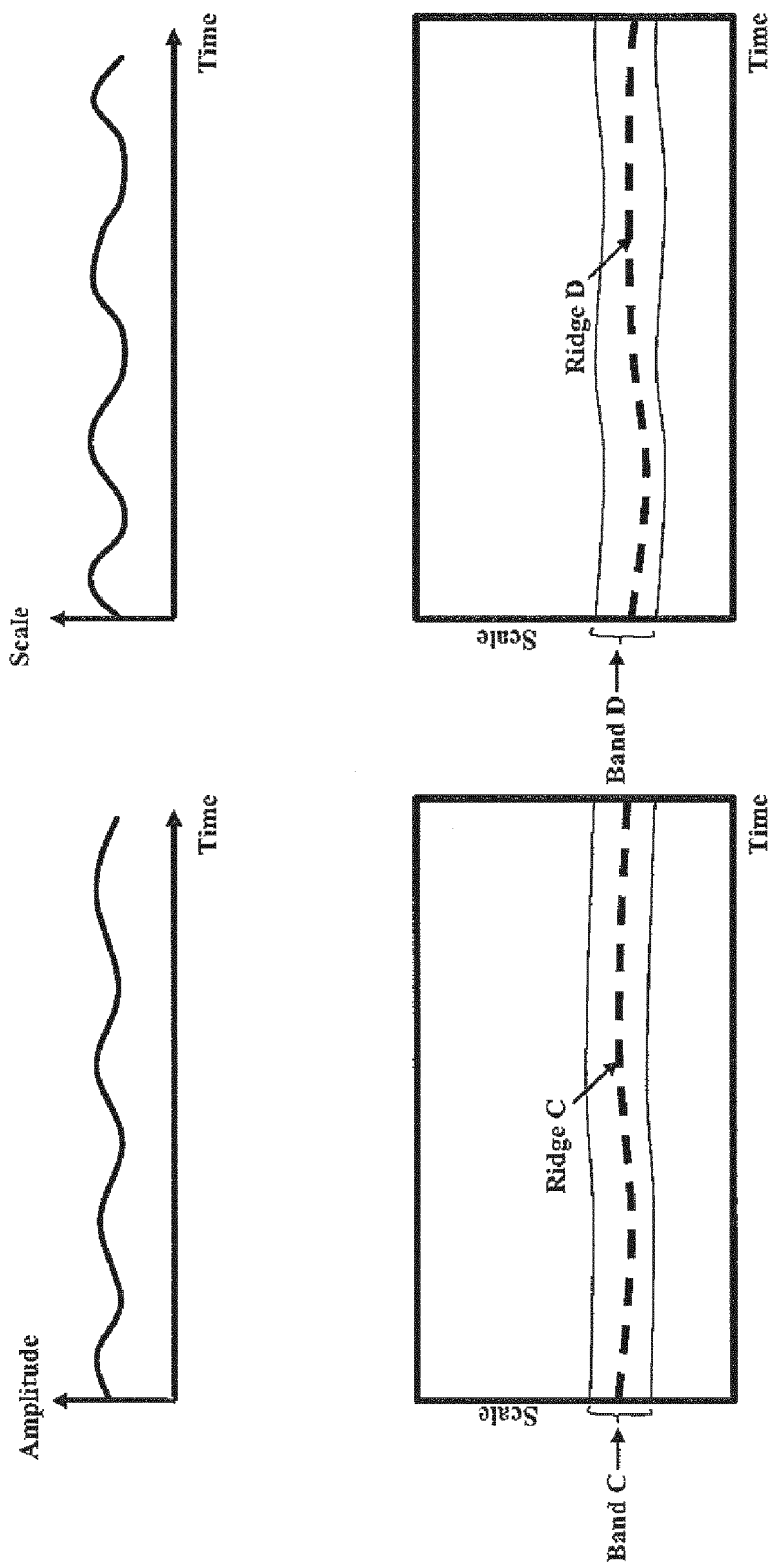
FIG. 3(d) shows an illustrative schematic of signals associated with a ridge in FIG. 3(c) and illustrative schematics of a further wavelet decomposition of these newly derived signals in accordance with an embodiment.

As discussed above, pertinent repeating features in the signal give rise to a time-scale band in wavelet space or a resealed wavelet space. For a periodic signal, this band remains at a constant scale in the time-scale plane. For many real signals, especially biological signals, the band may be non-stationary; varying in scale, amplitude, or both over time. FIG. 3(c) shows an illustrative schematic of a wavelet transform of a signal containing two pertinent components leading to two bands in the transform space, according to an embodiment. These bands are labeled band A and band B on the three-dimensional schematic of the wavelet surface. In this embodiment, the band ridge is defined as the locus of the peak values of these bands with respect to scale. For purposes of discussion, it may be assumed that band B contains the signal information of interest. This will be referred to as the "primary band". In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous (i.e., obscured, fragmented or missing). In this case, the ridge of band A may be followed in wavelet space and extracted either as an amplitude signal or a scale signal which will be referred to as the "ridge amplitude perturbation." (RAP) signal and the "ridge scale perturbation" (RSP) signal, respectively. The RAP and RSP signals may be extracted by projecting the ridge onto the time-amplitude or time-scale planes, respectively. The top plots of FIG. 3(d) show a schematic of the RAP and RSP signals associated with ridge A in FIG. 3(c). Below these RAP and RSP signals are schematics of a further wavelet decomposition of these newly derived signals. This secondary wavelet decomposition allows for information in the region of band B in FIG. 3(c) to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 3(c)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b:

$$x(t) = \frac{1}{C_g} \int_{-\infty}^{\infty} \int_0^{\infty} T(a,b) \frac{1}{\sqrt{a}} \psi\left(\frac{t-b}{a}\right) \frac{da\,db}{a^2} \quad (15)$$

which may also be written as:

$$x(t) = \frac{1}{C_g} \int_{-\infty}^{\infty} \int_0^{\infty} T(a,b) \psi_{a,b}(t) \frac{da\,db}{a^2} \quad (16)$$

where $C_g$ is a scalar value known as the admissibility constant. It is wavelet type dependent and may be calculated from:

$$C_g = \int_0^{\infty} \frac{|\hat{\psi}(f)|^2}{f} df \quad (17)$$

Figure 3E:
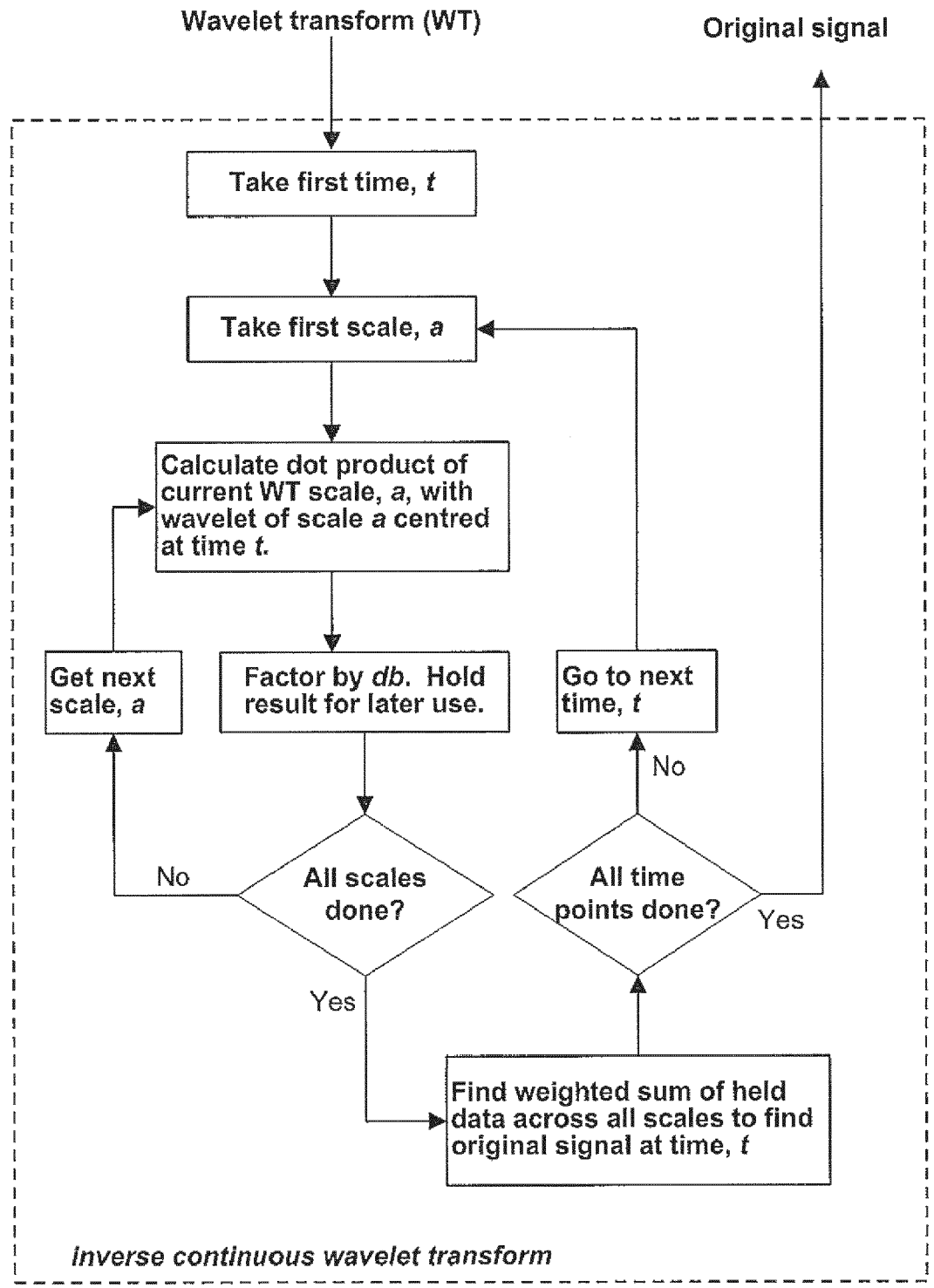
FIGS. 3(e) and 3(f) are flow charts of illustrative steps involved in performing an inverse continuous wavelet transform in accordance with embodiments.
Figure 3F:
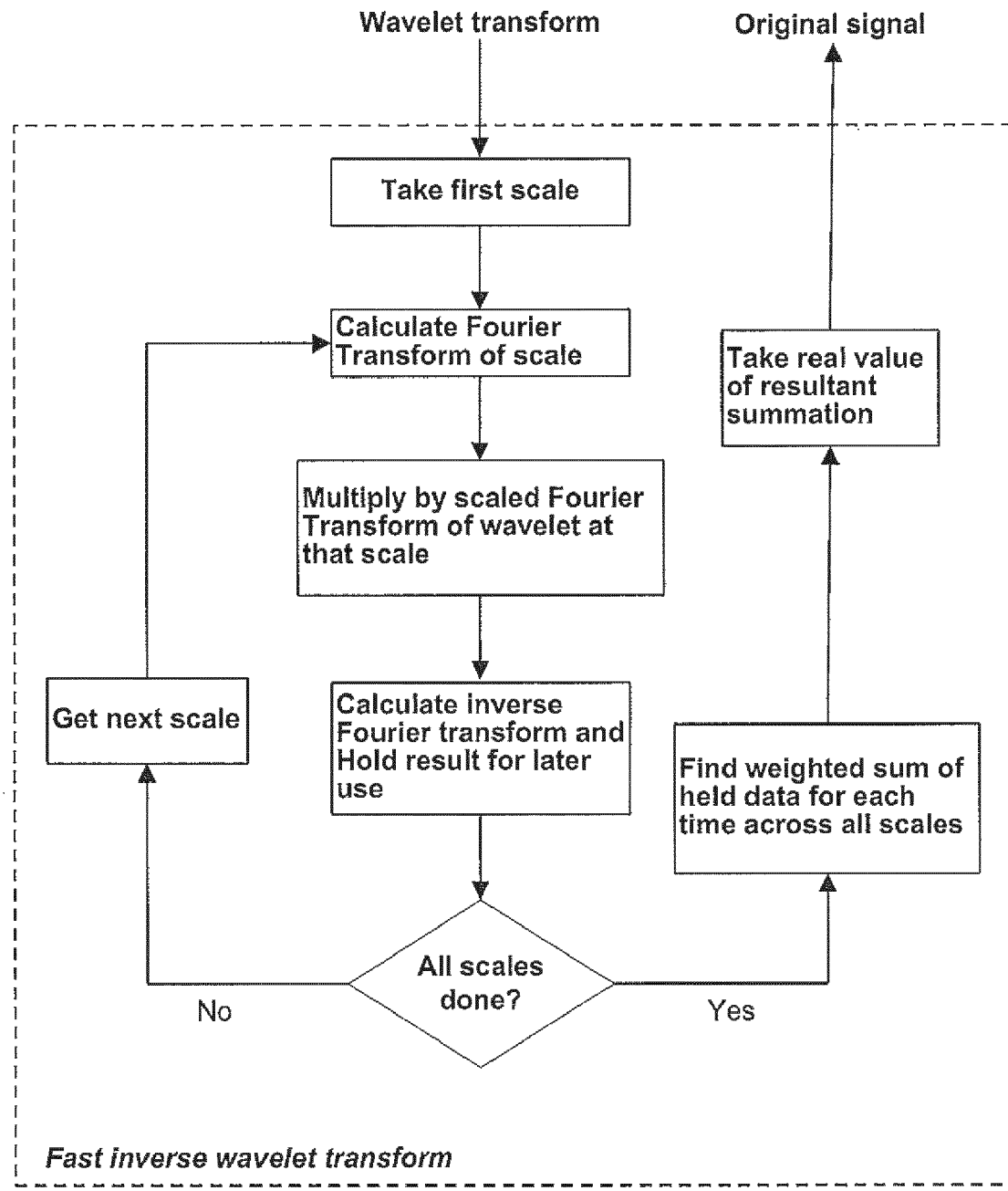

FIG. 3(e) is a flow chart of illustrative steps that may be taken to perform an inverse continuous wavelet transform in accordance with the above discussion. An approximation to the inverse transform may be made by considering equation (15) to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(f) is a flow chart of illustrative steps that may be taken to perform an approximation of an inverse continuous wavelet transform. It will be understood that any other suitable technique for performing an inverse continuous wavelet transform may be used in accordance with the present disclosure.

Figure 4:
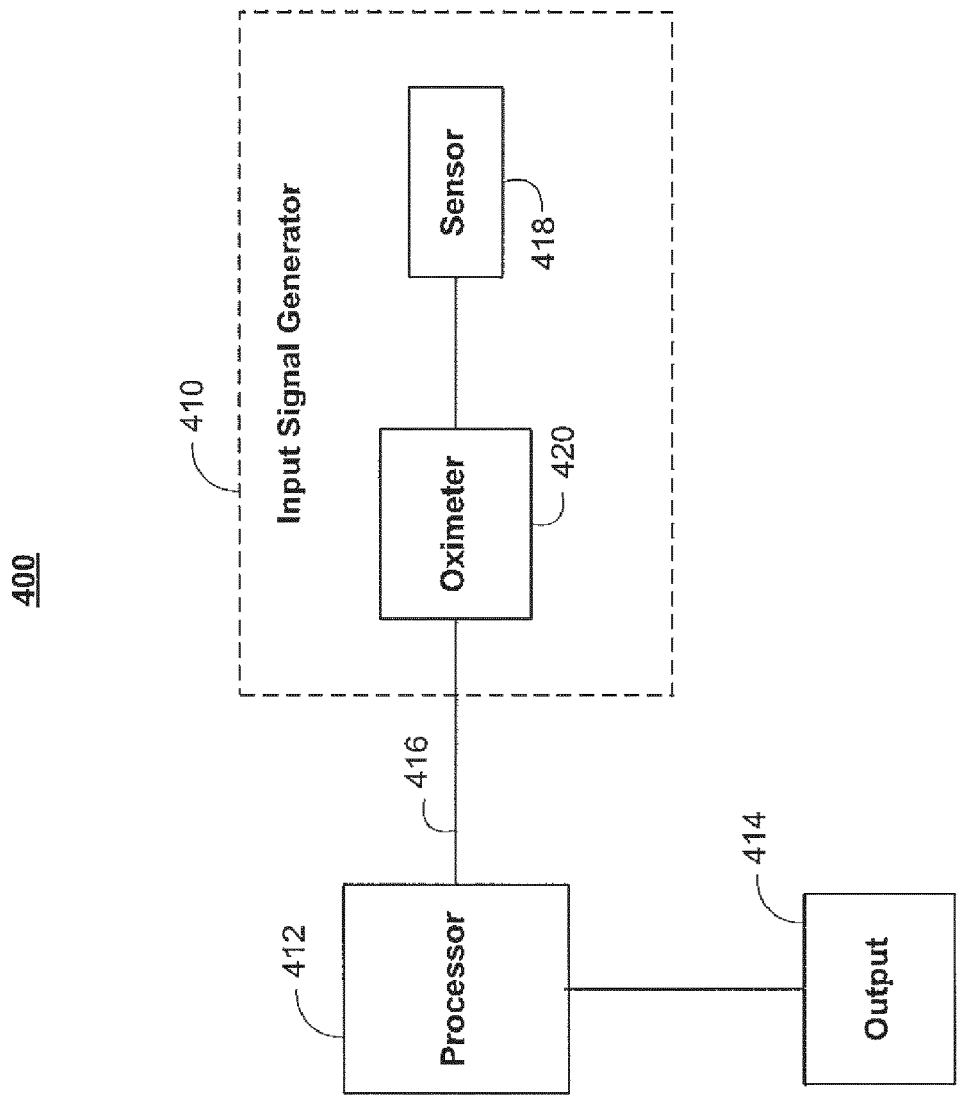
FIG. 4 is a block diagram of an illustrative continuous wavelet processing system in accordance with an embodiment.

FIG. 4 is an illustrative continuous wavelet processing system 400 in accordance with an embodiment. In this embodiment, input signal generator 410 generates an input signal 416. As illustrated, input signal generator 410 may include oximeter 420 coupled to sensor 418, which may provide as input signal 416, a PPG signal. It will be understood that input signal generator 410 may include any suitable signal source, signal generating data, signal generating equipment, or any combination thereof to produce signal 416. Signal 416 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In this embodiment, signal 416 may be coupled to processor 412. Processor 412 may be any suitable software, firmware, and/or hardware, and/or combinations thereof for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may perform the calculations associated with the continuous wavelet transforms of the present disclosure as well as the calculations associated with any suitable interrogations of the transforms. Processor 412 may perform any suitable signal processing of signal 416 to filter signal 416, such as any suitable band-pass filtering, adaptive filtering, closed-loop filtering, and/or any other suitable filtering, and/or any combination thereof.

Processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 412 to, for example, store data corresponding to a continuous wavelet transform of input signal 416, such as data representing a scalogram, in one embodiment, data representing a scalogram may be stored in RAM or memory internal to processor 412 as any suitable three-dimensional data structure such as a three-dimensional array that represents the scalogram as energy levels in a time-scale plane. Any other suitable data structure may be used to store data representing a scalogram.

In an embodiment, processor 412 may be coupled to output 414. Output 414 may be any suitable output device such as, for example, one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 400 may be incorporated into system 10 (FIGS. 1 and 2) in which, for example, input signal generator 410 may be implemented as parts of sensor 12 and monitor 14 and processor 412 may be implemented as part of monitor 14, according to an embodiment.

The band discrimination process of the present disclosure will now be discussed in reference to FIGS. 5-14.

In an embodiment, in connection with deriving useful information (e.g., clinical information) from one or more scale bands of interest front a scalogram, processor 412 or microprocessor 48 (FIG. 2) may perform an analysis to identify bands that are likely to contain the information sought as well as identify those bands that are likely due to noise or any other suitable phenomena. For example, in the context of a PPG signal obtained from a patient, taking the wavelet transform of the PPG signal and generating a scalogram from the transformed signal may yield information about, among other things, the pulse rate and breathing rate of the patient. In order to garner information about pulse rate and breathing rate, however, the scale bands of the scalogram associated with these rates may need to be identified from among a plurality of other bands that may appear on the scalogram. The present disclosure provides techniques for discriminating bands that are not of interest.

In an embodiment, a process to discriminate bands not of interest may rely on the fact that sometimes a band of interest may cause another band to occur that is modulated at a scale of the band of interest (e.g., the energy within the band is modulated). For example, when two bands are detected, if the first band is being modulated at a scale of the second band, then the first band (e.g., the band that is being modulated) may not be the band of interest. In the context of taking a wavelet transform of a PPG signal, a resulting scalogram may include bands that are modulated according at least in part to the pulse band scale, the breathing band scale, or both. These extraneous bands may make it difficult to identify the true pulse and breathing bands from the scalogram. The detection of the modulation may be performed in any suitable way.

In an embodiment, one process for detecting modulation may include examining maximum turning points in time along a scale. The process is referred to herein as the "mod-max discrimination" and is performed by a module referred to as a "mod-max discriminator." The mod-max discriminator, which may include software operated by processor 412 or microprocessor 48, shall be described with reference to FIGS. 5-9 in art embodiment, in the context of a PPG signal, the mod-max discriminator may be operated by microprocessor 48 (FIG. 2) operating in real time on samples from QSM 72 (FIG. 2) or from samples stored in ROM 52 or RAM 54 (FIG. 2). Alternatively, the PPG signals may be obtained from input signal generator 410, which may include oximeter 421) coupled to sensor 418, which may provide as input signal 416 (FIG. 4) PPG signals. In an embodiment, the PPG signals may be obtained from patient 40 using sensor 12 or input signal generator 410 in real time.

Figure 5:
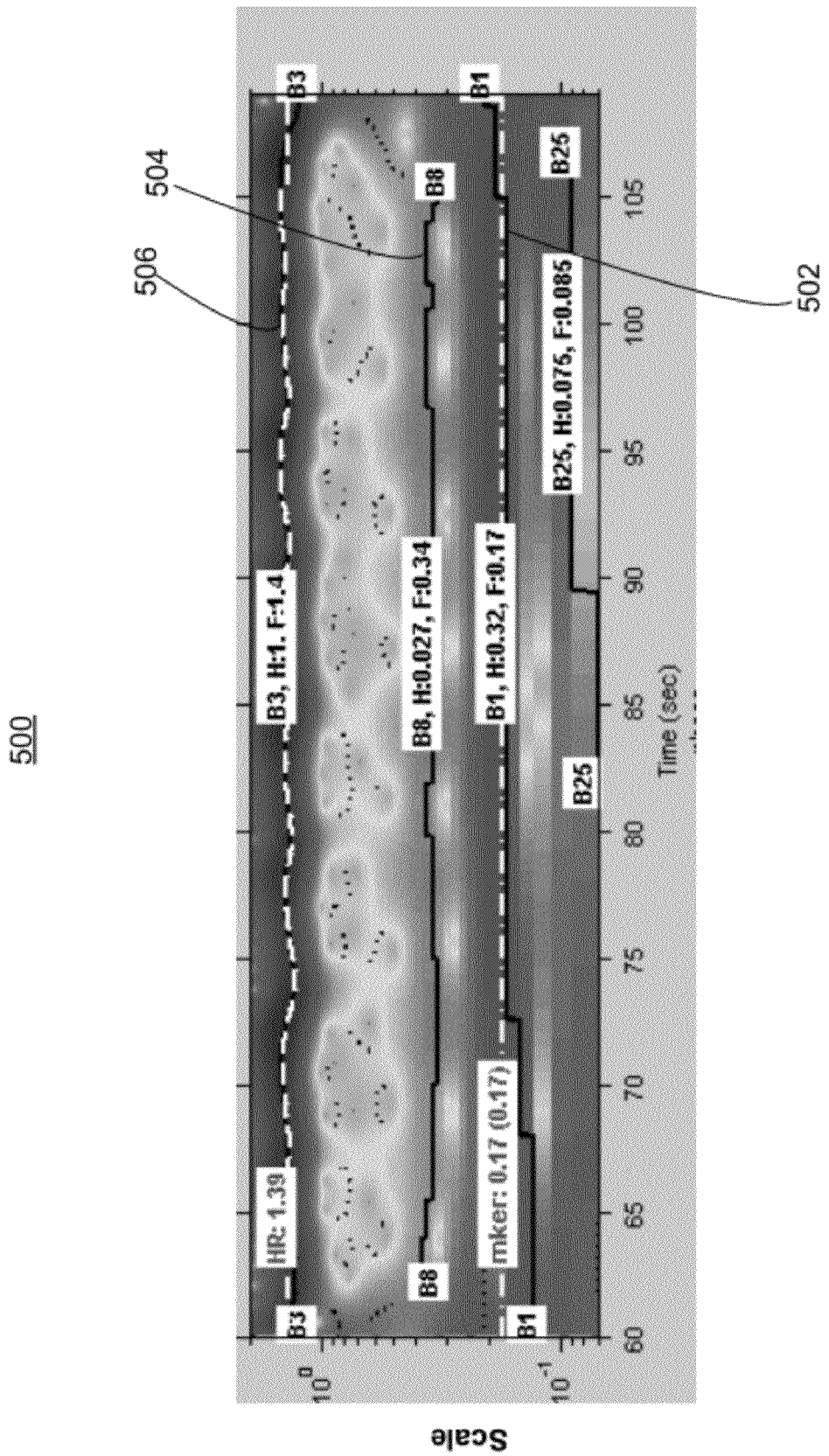
FIG. 5 shows a scalogram in accordance with some embodiments.

FIG. 5 shows a scalogram 500 in accordance with an embodiment. Scalogram 500 may include ridge candidates 502 and 504, each of which may be located within respective band candidates. In this disclosure, the term "ridge" shall refer to the amplitude peaks in a band formed over a temporal period in an embodiment, the discrimination technique may be used to determine whether a first band is causing a second band to appear in the scalogram and be modulated at the scale of the first band. For example, ridge 502 may be a source ridge candidate (e.g., a ridge that may be considered a possible ridge of interest, such as a breathing ridge in the context of a wavelet transform of a PPG signal obtained from patient 40) and ridge 504 may be a profile ridge candidate (e.g., a ridge that may be "attached" to the band of interest) or considered as a possible ridge being modulated in profile at the scale of the band of interest). In an embodiment, the band of interest (e.g., a pulse band in the context of the wavelet transform of the PPG signal) may correspond to ridge 506.

Figure 6:
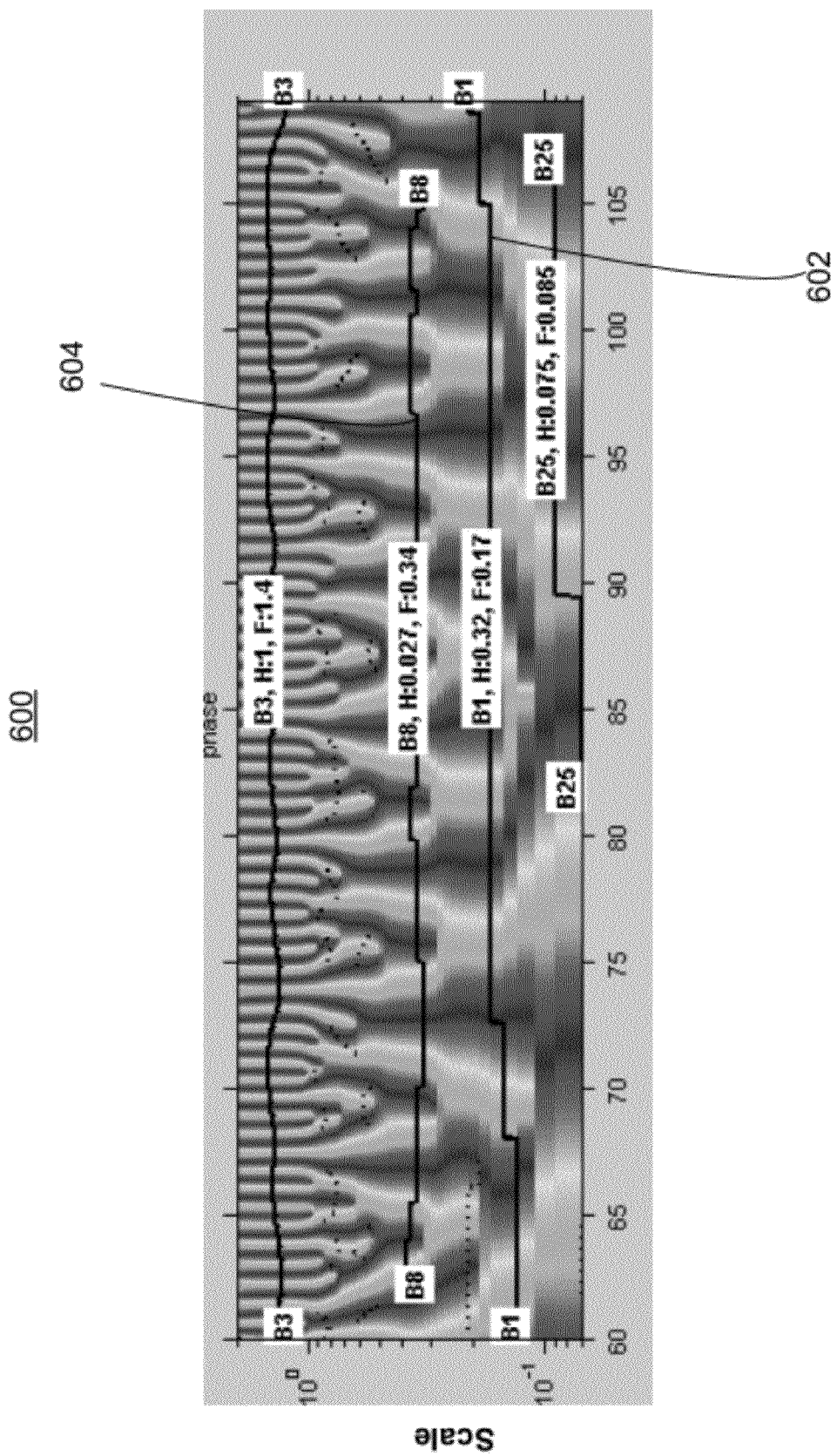
FIG. 6 shows a mapping of the instantaneous phase gradient in accordance with an embodiment.

FIG. 6 shows a mapping 600 of the instantaneous phase gradient loci of ridges 502 and 504 in accordance with an embodiment. The map may include any suitable axes, such as scale being plotted as a function of phase. The mod-max discriminator may first map the instantaneous phase (unwrapped) gradient (IPG) along the loci of each of ridges 602 and 604 that may correspond to ridges 502 and 504. The IPG may be defined as the mean of the ratios of the change in unwrapped phases of two ridges. In an embodiment, the IPG may be generated by: (1) determining the unwrapped phases associated with ridges 602 and 604 and placing the unwrapped phase determinations in two respective vectors; (2) calculating the differences for each vector with respect to time so as to have two vectors of changes in unwrapped phase; (3) dividing one vector of changes in unwrapped phase (element-wise) by the other; and (4) determining the mean value of the ratios resulting from the previous dividing step. Generally, if the IPG value is above 2.0, there may be a high probability that the candidate ridge (e.g., ridge 504) is an attached ridge. In an embodiment, an instantaneous phase ratio (IPR) may then be computed as the ratio of the upper ridge 604 IPG to the lower ridge 602 IPG. In an embodiment, an IPR value equal to or greater than 2.0 may cause the mod-max discriminator to continue the discrimination process. For example, an IPG may be a measure of the recurrence rate of certain features of a scalogram, or a rate of phase cycling. If the IPG of upper ridge 604 is divided by the IPG of lower ridge 602, and the resulting IPR includes a value equal to 2.0, then one ridge may occur at a scale value that is twice the scale value of the other ridge, and may indicate that the presence of one ridge is caused by the presence of the other ridge. It will be understood that any other suitable IPR value thresholds may be used, either lower than or greater than 2.0.

Figure 7:
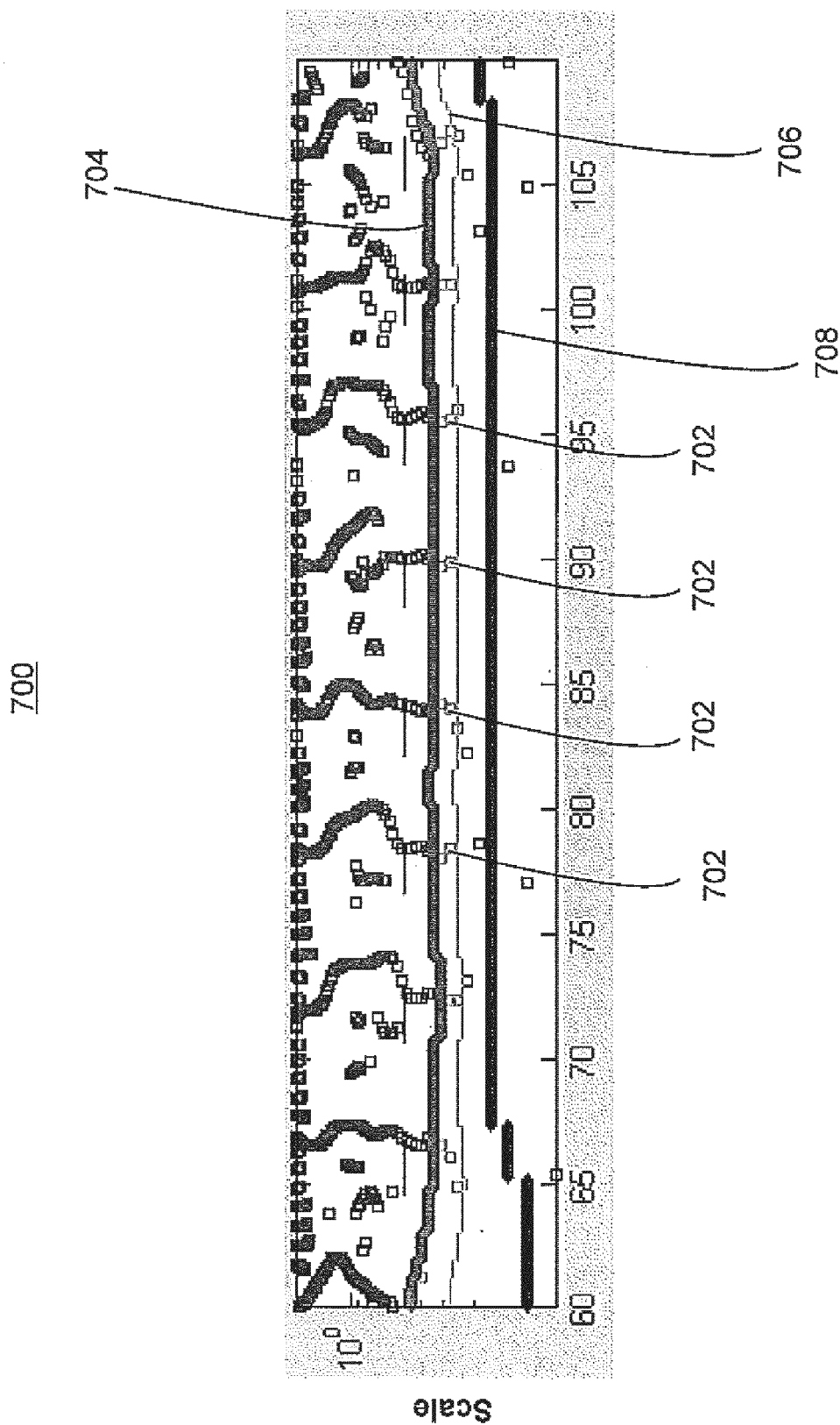
FIG. 7 shows a distribution of mod-max points in accordance with an embodiment.

The mod-max discriminator may then consider the distribution of mod-max points, as shown, for example, in FIG. 7. The mod-max points 702 may include the loci of the maxima of the modulus of scalogram 500 with respect to time, which may include vertical maxima lines on the scalogram, or the mod-max points 702 may include the horizontal ridges 704 and 708 which may be defined as the loci of maxima with respect to scale. The mod-max points 702, or the maximum turning points in time along a particular scale from scalogram 500, may be distributed in an inter-ridge region that may be bounded between the upper ridge loci 704 and a lower boundary 706 that may be located half way between the upper and lower ridge 708 of the ridge-pair.

Figure 8:
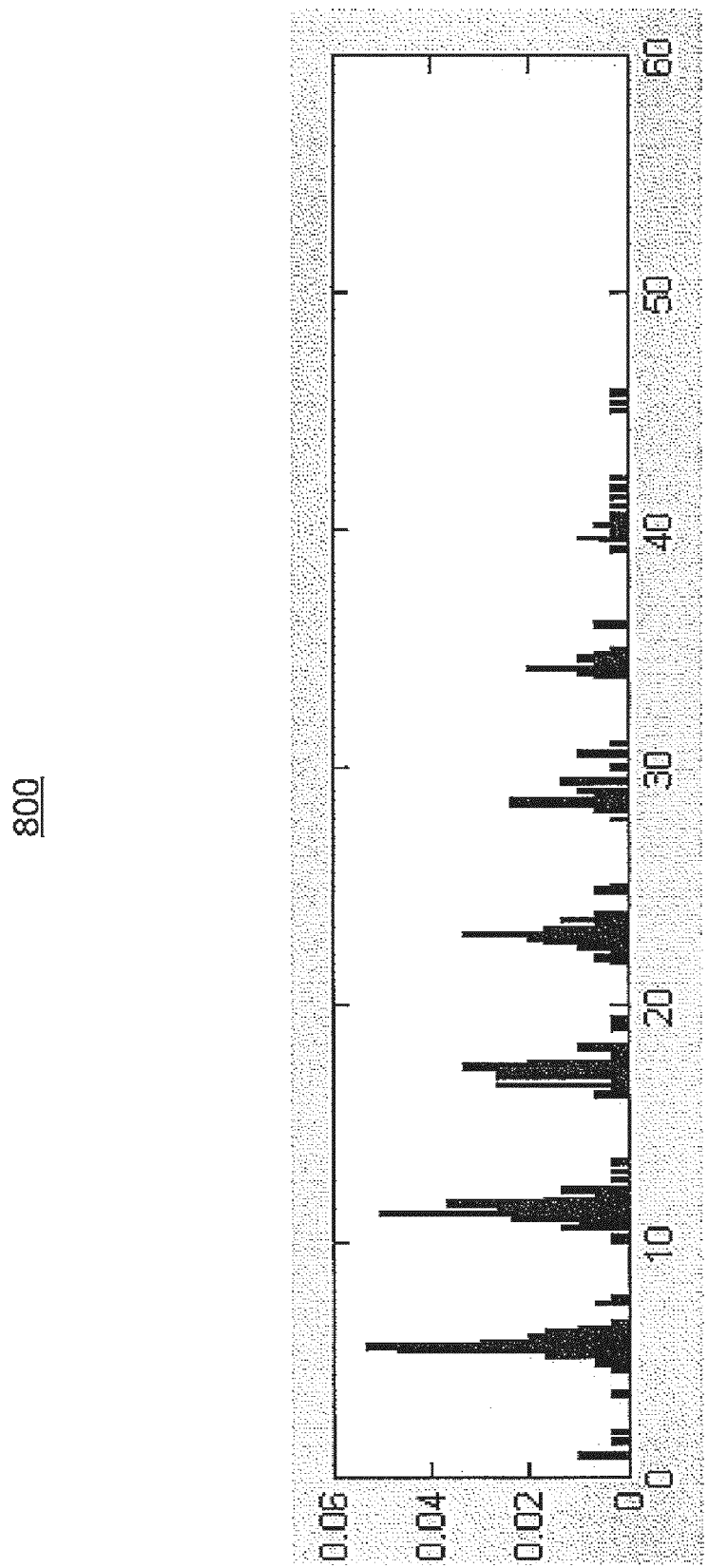
FIG. 8 shows a population histogram in accordance with an embodiment.

In an embodiment, a population histogram of the inter-point distribution of mod-max points 702 may be generated by processor 412 or microprocessor 48. FIG. 8 shows a population histogram 800 in accordance with some embodiments. The inter-point distribution may represent dt values that may be computed as the difference in time for each mod-max point 702 to all other mod-max points. A peak on histogram 800 may indicate that a particular dt value occurs frequently within the inter-point distribution.

Figure 9:
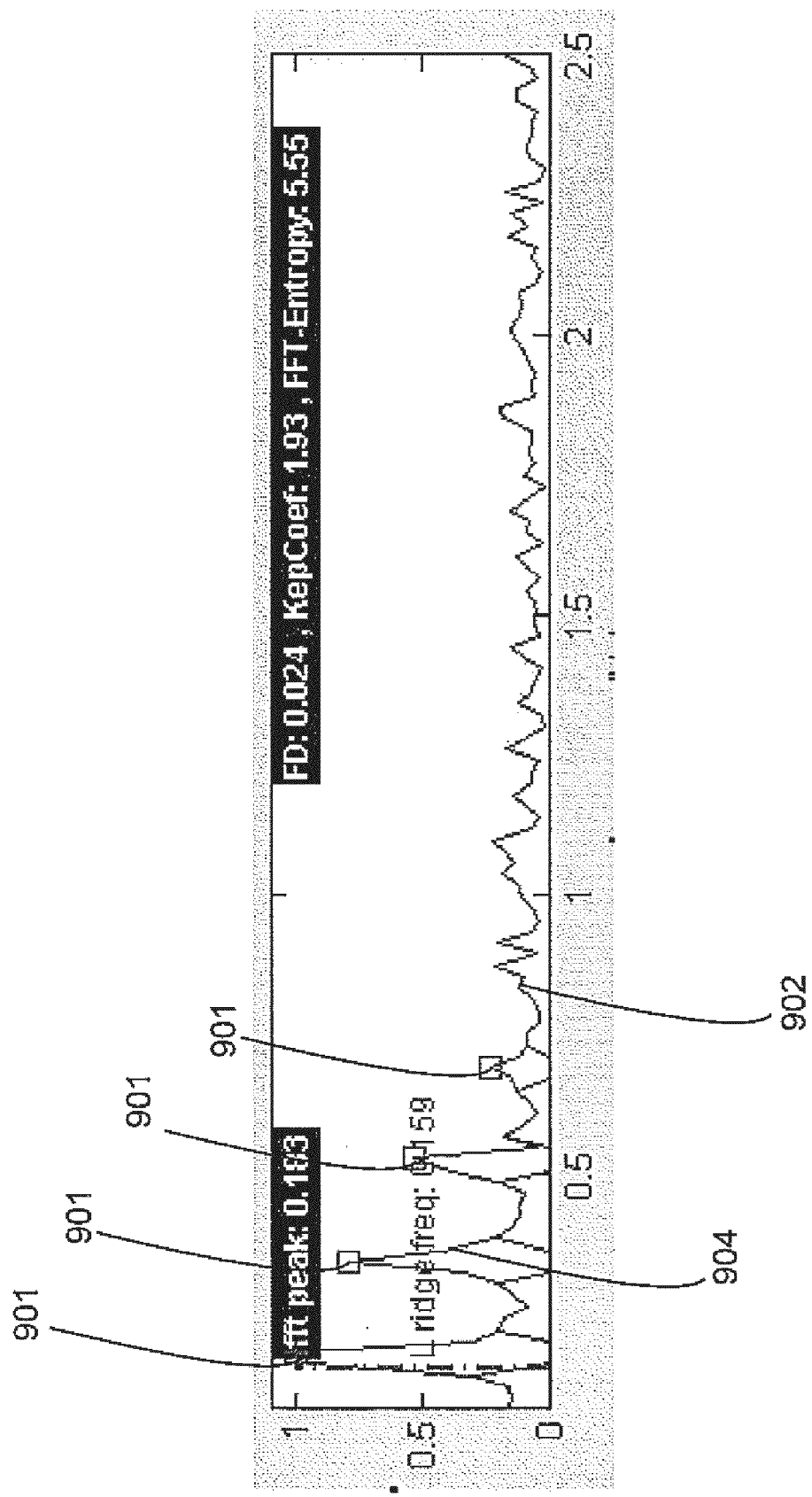
FIG. 9 shows a Fast Fourier Transform of a dt population vector in accordance with an embodiment.

In an embodiment, a dt population vector may be derived by the mod-max discriminator from the population histogram in FIG. 8, For example, the dt population vector may be derived by interrogating every mod-max point 702 and generating a histogram of distances from each mod-max point 702 to every other mod-max point 702 for each mod-max point 702 of FIG. 7. In an embodiment, one or more mod-max points 702 may be removed from interrogation, including for example, those dt values measured between points that may be proximal in time (e.g., points that may correspond to low-energy or low-scale background noise). The mod-max discriminator may then compute a Fast Fourier Transform (FFT) of the dt population vector. FIG. 9 shows a FFT of the dt population vector in accordance with an embodiment. In an embodiment, the FFT peak and its most dominant (e.g., three) harmonics may be identified (shown in FIG. 9 as squares 901) by the mod-max discriminator and removed from the FFT vector. The values of the harmonic points indicated by squares 901 may be stored in a FFT_H vector, as shown by plot 904. The remaining vector may be stored in a FFT_R vector, as shown by plot 902.

In an embodiment, a KepCoef coefficient may thereafter be computed as the sum of FFT_H vector 904 divided by the sum of FFT_R vector 902. The KepCoef coefficient may indicate the likelihood that two ridges (e.g. ridges 502 and 504) are attached from the relative strengths of the harmonic (H) transform and residual (R) transform (e.g., the transform that has the harmonic data removed). A high value for the KepCoef coefficient may point to a strong harmonic response, which may indicate a regular modulation of the values of scalogram 500 between ridges 502 and 504 and, therefore, a higher likelihood that ridges 502 and 504 may be attached.

In an embodiment, an entropy coefficient may also be computed to evaluate whether the signal information (e.g., the PPG signal) that creates ridge 502 may be intermittent, the intermittency of which may indicate the presence of a (modulating) profile ridge 504. In some embodiments, either the KepCoef coefficient or the entropy coefficient, or a combination of these coefficients, may be used to establish the validity of the profile-component, or the existence of modulation of the profile band 504 at the scale of the source band 502. Where the mod-max discriminator determines that modulation may exist, a confidence level of either high or low also may be set.

Figure 10:
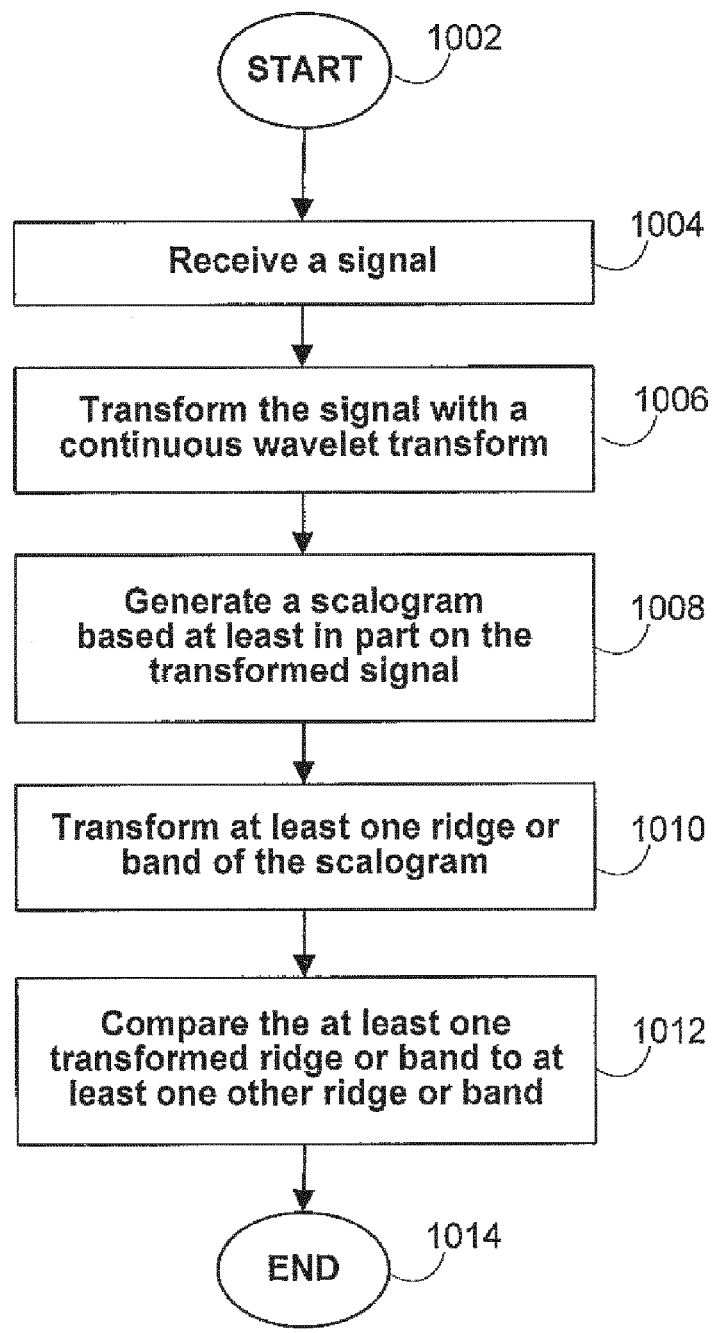
FIG. 10 is a flowchart of an illustrative process for detecting modulation, of a band in accordance with an embodiment.

In another embodiment, modulation of one band according at least in part to a scale of another band may be detected by, for example, taking an FFT, or any other suitable transform including a secondary wavelet transform, of the amplitude modulation of a ridge or band and comparing the result to the scale of the other ridge, ridges, band or bands. If the scale of modulation matches the scale, then the candidate ridge or band may be modulated at the scale of the other ridge and may therefore not be a ridge or band of interest. FIG. 10 is a flowchart of illustrative steps for detecting modulation of a band in accordance with an embodiment, Process 1000 may begin at step 1002. At step 1004, as signal (e.g., a PPG signal) may be received from any suitable source (e.g., patient 40) using any suitable method. For example, a PPG signal may be obtained from sensor 12 that may be coupled to patient 40. Alternatively, the PPG signal may be Obtained from input signal generator 410, which may include oximeter 420 coupled to sensor 418, which may provide as input signal 416 (FIG. 4) a PPG signal. In an embodiment, the PPG signal may be obtained from patient 40 using sensor 12 or input signal generator 410 in real time. In an embodiment, the PPG signal may have been stored in ROM 52, RAM 52, and/or QSM 72 (FIG. 2) in the past and may be accessed by microprocessor 48 within monitor 14 to be processed.

In an embodiment, at step 1006, the signal may be transformed in any suitable manner. For example, a PPG signal may be transformed using a continuous wavelet transform as described above with respect to FIG. 3(c). In an embodiment, at step 1008, a scalogram may be generated based at least in part on the transformed signal. The scalogram of a PPG signal may be generated as described above with respect to FIGS. 3(a) and 3(b). For example, processor 412 or microprocessor 48 may perform the calculations associated with the continuous wavelet transform of the PPG signal and the derivation of the scalogram.

In an embodiment, at step 1010, at least one ridge or band of the scalogram generated in step 1006 may be further transformed using any suitable transform. For example, the amplitude modulation of a ridge or band (e.g., the candidate ridge or band) may be transformed using a Fast Fourier Transform, a secondary wavelet transform, or any other suitable transform. In an embodiment, at step 1012, the scale of the ridge or band that may have been further transformed at step 1010 may be compared to the characteristic scale of another ridge or band (e.g., the source ridge or band). If the scale of the modulation (e.g., the scale of the transformed candidate ridge or band) matches the characteristic scale of the source ridge or band, then the candidate ridge or band may be modulated at the scale of the source ridge or band, and may therefore not be a ridge or band of interest. Process 1000 may advance to step 1014 and end.

In another embodiment, modulation of one band according at least in part to scales of another band may be detected by filtering the original PPG signal at the scales under investigation (e.g., the scales that may be associated with the band or bands of interest). For example, in one embodiment, by filtering the original PPG through a narrow band-pass fitter that may be centered on the scale of each of the ridges believed to be of interest, the outcomes of the filtering for each scale may be compared. Modulation may be detected if the outcomes match. Also, when filtering out the pulse band, the resultant, filtered, PPG signal should have a dominant period of oscillation of about the breathing rate (i.e., corresponding to the scale of the breathing ridge).

Figure 11A:
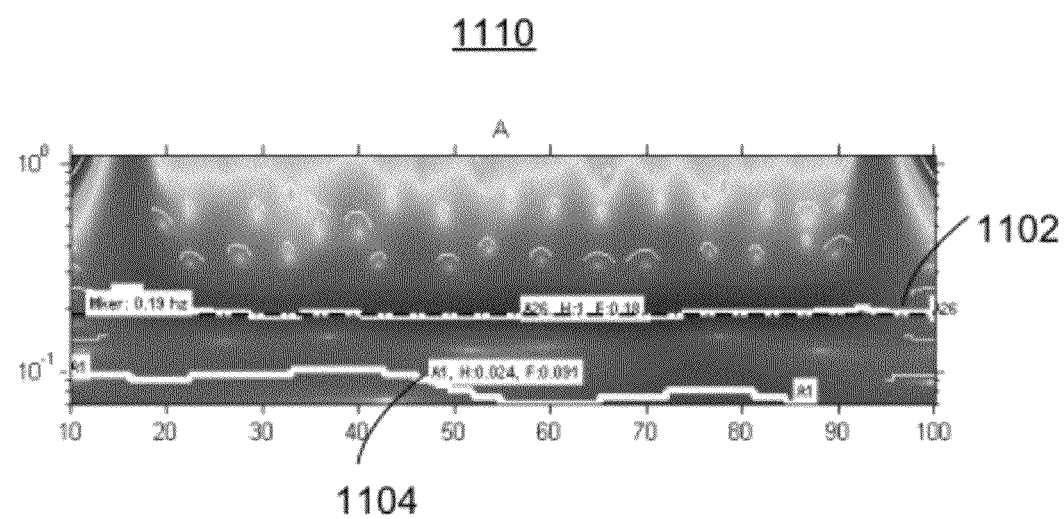
FIG. 11(a) shows a scalogram in accordance with an embodiment.
Figure 11B:
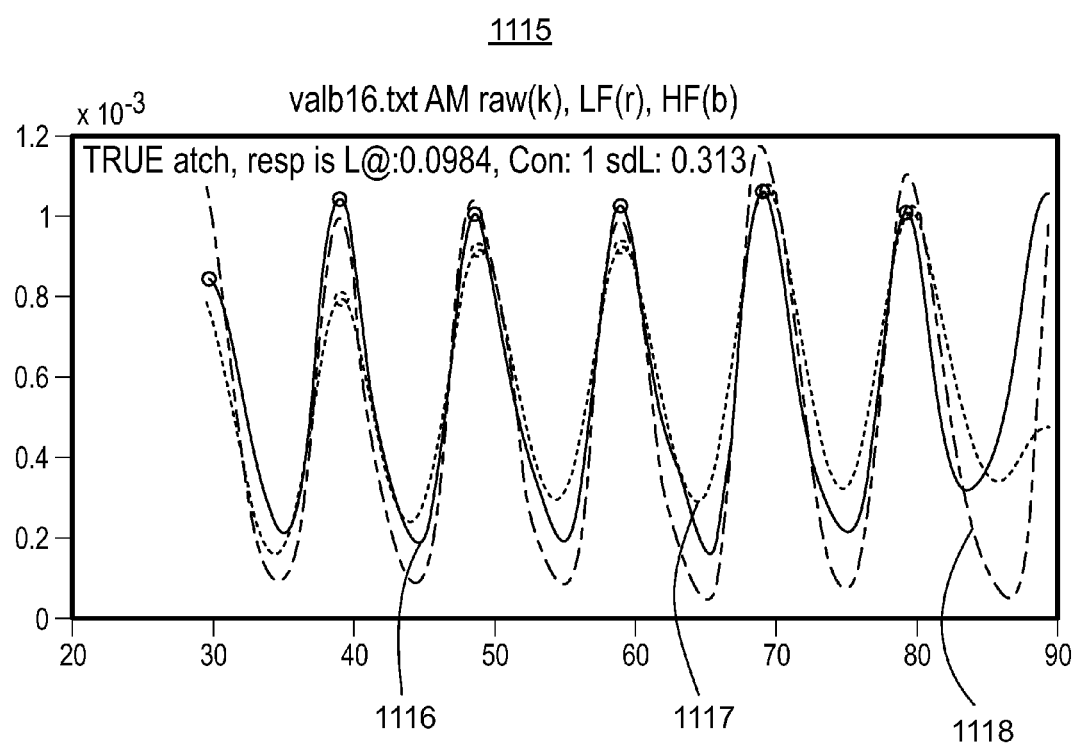
FIG. 11(b) shows a mapping of amplitude modulation in accordance with an embodiment.

FIG. 11(a) shows a scalogram in accordance with an embodiment. Two main ridges, ridge 1102 and ridge 1104, may be evident in scalogram 1110. Scalogram 1110 may represent the amplitude modulation of a pulse band in the wavelet transform of an original PPG signal. By filtering the original PPG signal around scales associated with ridges 1102 and 1104 using any suitable filter (e.g., a band-pass filter centered on the scale of each of ridges 1102 and 1104), a second plot of the filtered signal(s) may be analyzed for modulation. FIG. 11(b) shows a mapping 1115 of amplitude modulation, in accordance with an embodiment. Plot 1115 may include a plot 1116 of the amplitude modulation of the PPG signal filtered at the scale value of ridge 1102 and a second plot 1117 of the amplitude modulation of the PPG signal filtered at the scale value of ridge 1104. Plot 1115 also may include a plot 1118 of the original PPG signal without a filter applied at a particular scale. The three plots may exhibit the same period of amplitude modulation, which may be the modulation period of lower ridge 1104. Thus, the breathing rate may be associated with the scale of lower ridge 1104.

Figure 11C:
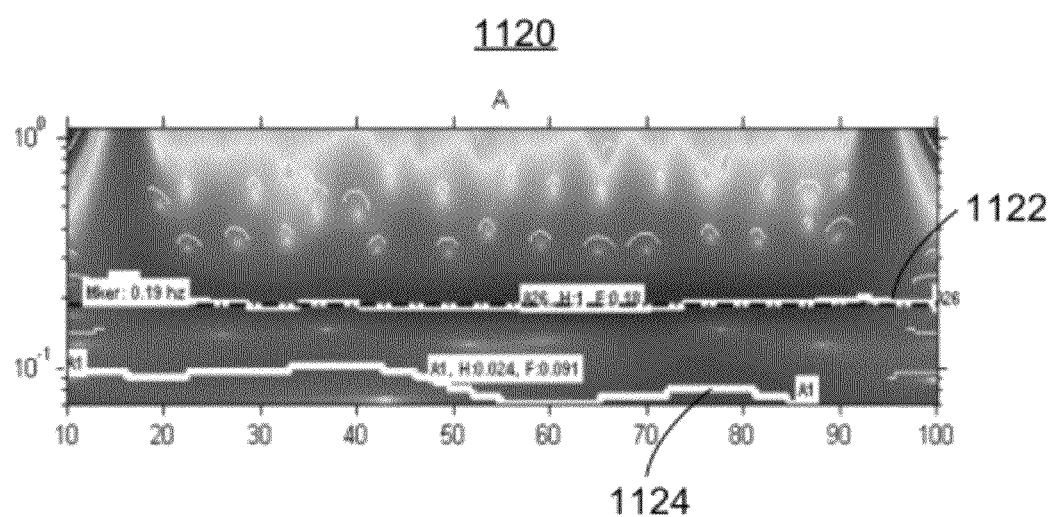
FIG. 11(c) shows a scalogram in accordance with an embodiment.
Figure 11D:
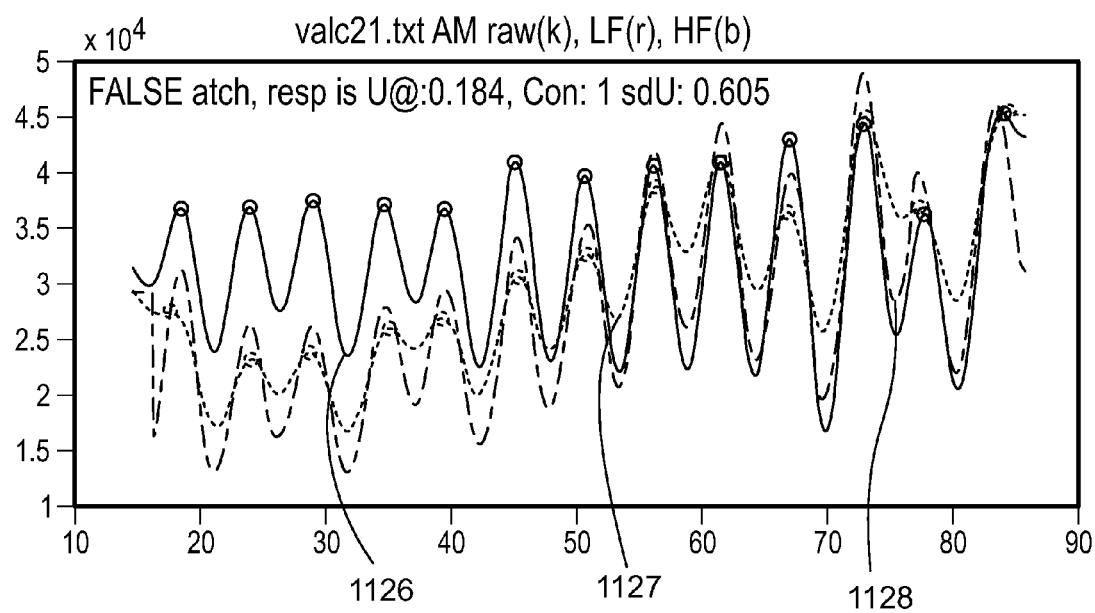
FIG. 11(d) shows a mapping of amplitude modulation in accordance with an embodiment.
Figure 11E:
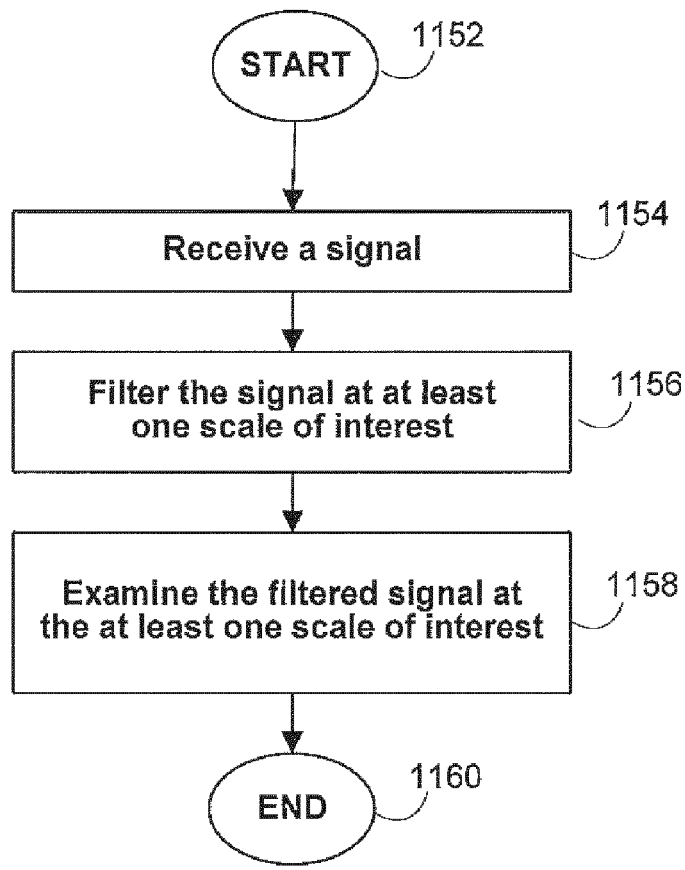
FIG. 11(e) is a flowchart of an illustrative process for filtering a signal to detect modulation in accordance with an embodiment.

FIG. 11(c) shows a scalogram in accordance with an embodiment. Two main ridges, ridge 1122 and ridge 1124, may be evident in scalogram 1121. As with scalogram 1110, scalogram 1120 may represent the amplitude modulation of a pulse band in the wavelet transform of an original PPG signal. By filtering the original PPG signal around scales associated with ridges 1122 and 1124 using any suitable filter (e.g., a band-pass filter centered on the scale of each of ridges 1122 and 1124), a second plot of the filtered signal(s) may be analyzed for modulation. FIG. 11(d) shows a mapping 1125 of amplitude modulation in accordance with an embodiment, Plot 1125 may include a plot 1126 of the amplitude modulation of the PPG signal filtered at the scale value of ridge 1122 and a second plot 1127 of the amplitude modulation of the PPG signal filtered at the scale value of ridge 1124. Plot 1125 also may include a plot 1128 of the original PPG signal without a filter applied at a particular scale. The three plots may exhibit the same period of amplitude modulation, which may be the modulation period of upper ridge 1122. Thus, the breathing rate may be associated with the scale of upper ridge 1122.

FIG. 11(*e*) is a flowchart of an illustrative process for filtering a signal to detect modulation in accordance with an embodiment. Process 1150 may begin at step 1152. At step 1154, a signal (e.g., a PPG signal) may be received from any suitable source (e.g., patient 40) using any suitable method. For example, a PPG signal may be obtained from sensor 12 that may be coupled to patient 40. Alternatively, the PPG signal may be obtained from input signal generator 411), which may include oximeter 420 coupled to sensor 418, which may provide as input signal 416 (FIG. 4) a PPG signal. In an embodiment, the PPG signal may be obtained from patient 40 using sensor 12 or input signal generator 410 in real time. In an embodiment, the PPG signal may have been stored in ROM 52, RAM 52, and/or QSM 72 (FIG. 2) in the past and may be accessed by microprocessor 48 within monitor 14 to be processed.

In an embodiment, at step 1156, the signal may be filtered using any suitable filtering method. For example, a PPG signal may be filtered through a narrow band-pass filter that may be centered on the scale of a ridge of interest (e.g., a source ridge, ridge 502 of FIG. 5, or ridges 1102 and 1104 of FIG. 11(*a*)). The PPG signal may be filtered through any suitable additional number and type of filters that may be centered on the scales of different ridges of interest. In an embodiment, at step 1158, the signals resulting from being passed through each of the applied filters may be examined, including as described above with respect to FIGS. 11(*a*)-11(*d*). For example, the filtered signals may be compared to determine whether the filtered signals exhibit the same period of amplitude modulation. Alternatively or additionally, the original signal may also be compared to the filtered signal(s). If the filtered signals match (e.g., exhibit the same period of modulation), then modulation may exist at the examined scale of interest. Process 1150 may advance to step 1160 and end.

In another embodiment, discrimination may be performed by locating "coupled bands." Coupling may be a predictable feature in the wavelet transform space, although it may be unrelated to the wavelet transform itself. Coupling may be caused by the modulation of two dominant ridge scales of the signal, and the modulation may include a product in the time domain that may lead to a convolution of the two dominant ridge scales in the wavelet transform (e.g., scalogram) domain. A coupled band may occur, for example, at a scale location between two bands. The coupled band is typically at a lower amplitude than the amplitude of the two neighboring bands.

Figure 12:
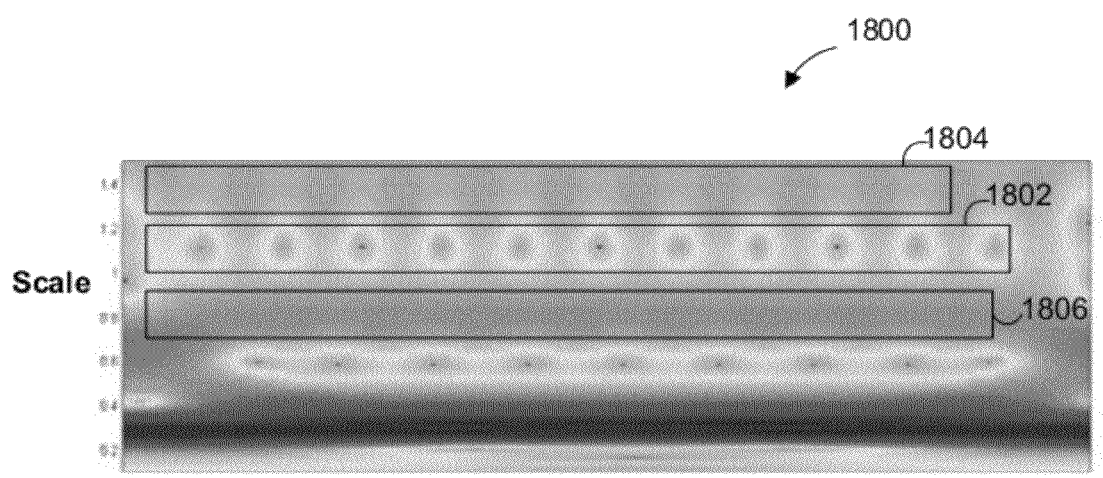
FIG. 12 shows a coupled band in accordance with an embodiment.

FIG. 12 shows coupled band 1802 formed between bands 1804 and 1806 on scalogram 1800. Because coupled bands may be an unintentional result of a continuous wavelet transform, they may be discriminated in any suitable manner, in an embodiment, process 412 or microprocessor 48 may include any suitable software, firmware, and/or hardware for locating and discriminating such coupled bands, in an embodiment, in the context of a PPG signal transformed by a continuous wavelet transform, the resulting scalogram (e.g., scalogram 1800) may include a pulse band 1804 and a breathing band 1806 at a lower scale than the pulse band. A coupled band 1802 may be created unintentionally between the pulse band and the breathing band, thus making it difficult to determine which are the true pulse and breathing bands. In an embodiment, another coupled band may exist above pulse band 1804, and one or more ridges may be located below breathing band 1806 as a result of the coupling phenomena.

A coupled band may be detected in any suitable manner. In an embodiment, the coupled band may be detected by processor 412 or microprocessor 48 by comparing the coupled bands energy amplitude along its scales to the time-wise corresponding energy amplitudes of one or more neighboring bands or ridges. For example, a moving average computed from the energies of neighboring bands or ridges may be used to determine a threshold against which the candidate band's (or ridge's) energy may be compared. The energy of the candidate band may be expected to be below the moving average of the energies of the neighboring bands. Any other suitable analysis of a candidate band's energy may be used to determine whether it is a band of interest.

In an embodiment, the scale modulation, amplitude modulation, or both of the candidate band or ridge may be compared to that of its neighboring bands or ridges to determine if it is a coupled band. This may take the form of comparing the scales at which these neighboring bands may occur and comparing their relative positions with those that might be expected if the bands were coupled. For example, if one signal oscillating at a first rate is modulated in amplitude at a second rate, then it may be expected that a third ridge would appear at the difference between the scale representing the first rate and the scale representing the second rate.

Figure 13:
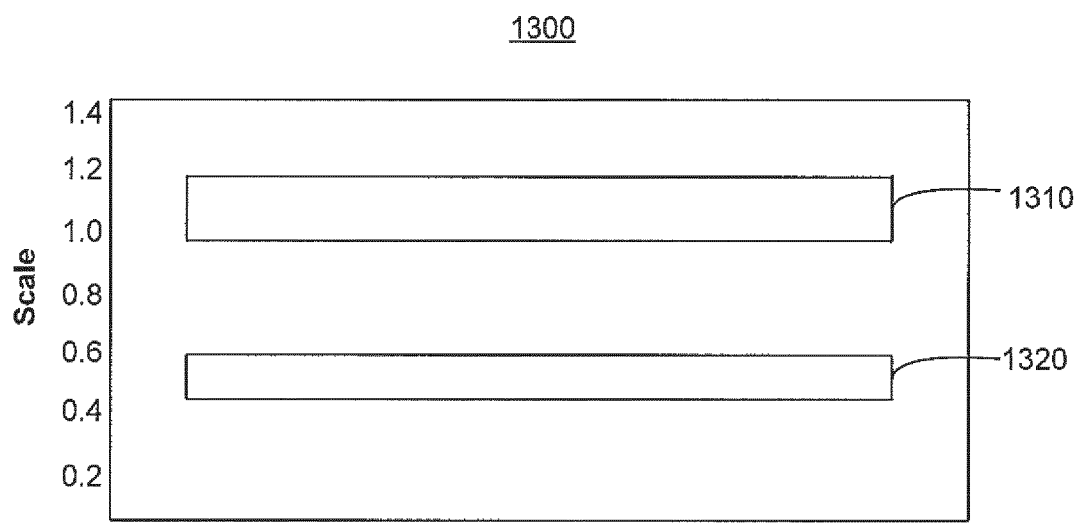
FIG. 13 shows a half-scale band in accordance with an embodiment.

In an embodiment, discrimination may be performed by identifying phenomena on a scalogram that will be referred to herein as "band half scales." This phenomenon may cause a dominant (e.g., high energy) band, such as the pulse band 1804 in the context of a PPG signal, to produce a lower energy band at about half the scale of the dominant band. Band half scales may be detected by processor 412 or microprocessor 48 by examining the scalogram at scales that are about half of the scales associated with detected high energy bands. FIG. 13 shows a half-scale band in accordance with some embodiments. Scalogram 1300 may include any suitable number of bands, such as bands 1310 and 1320. Band 1310, which may be the same as band 1804, may be the dominant band of interest of scalogram 1300 and may have clinical relevance (e.g., may be related to a patient's pulse rate). Band 1310 may produce a lower energy band 1320 at a scale value approximately half of the scale value of dominant band 1310. By examining scalogram 1300 at scales that are approximately half of the value of the anticipated scale(s) of interest, band 1320 may be identified and discriminated as not being of interest.

After a band has been identified as not being of interest (whether by the techniques discussed herein, or by any other suitable technique), that band may be discriminated. For example, when a band is discriminated, that band may be marked or masked by processor 412 or microprocessor 48 such that any further processing of bands of interest, such as a pulse band and/or a breathing band in the context of a PPG signal, may ignore the marked bands (e.g., the ranges of scales within the scalogram that may be associated with the bands) or otherwise treat them accordingly. For example, the bands to be discriminated may be removed from the scalogram by replacing them with energy bands of predetermined energy levels (e.g., a constant amplitude of zero) or with energy bands derived dynamically according at least in part to, for example, features of the scalogram (e.g., according at least in part to a running average across a temporal period and/or scale range of the scalogram).

Figure 14:
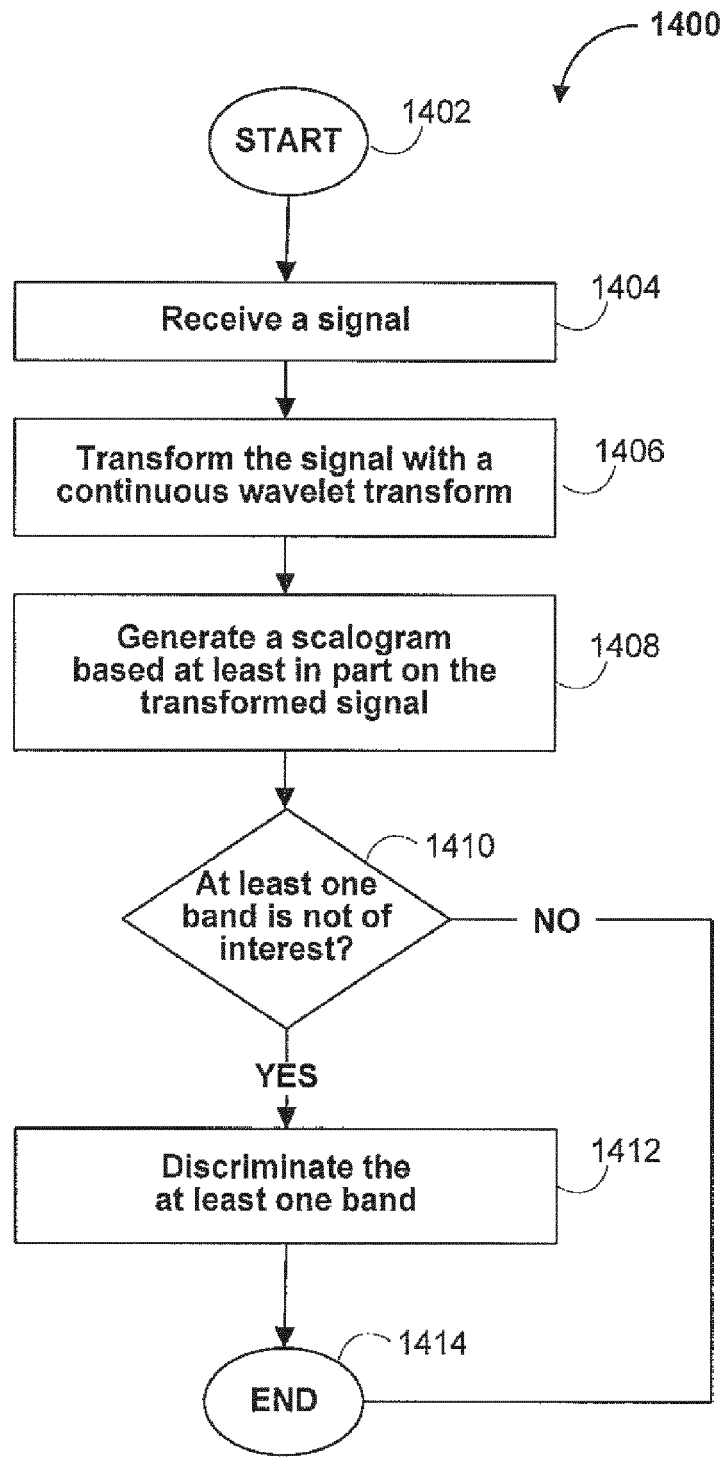
FIG. 14 is a flowchart of an illustrative process for discriminating at least one band from a scalogram derived at least in part from a PPG signal in accordance with an embodiment.

FIG. 14 is a flowchart of an illustrative process for discriminating at least one band from a scalogram derived at least in part from a signal in accordance with an embodiment. Process 1400 may begin at step 1402. At step 1404, a signal (e.g., a PPG signal) may be received from any suitable source (e.g., patient 40) using any suitable method. For example, a PPG signal may be obtained from sensor 12 that may be coupled to patient 40. Alternatively, the PPG signal may be obtained from input signal generator 410, which may include oximeter 420 coupled to sensor 418, which may provide as input signal 416 (FIG. 4) a PPG signal. In an embodiment, the PPG signal may be obtained from patient 40 using sensor 12 or input signal generator 410 in real time. In an embodiment, the PPG signal may have been stored in ROM 52, RAM 52, and/or QSM 72 (FIG. 2) in the past and may be accessed by microprocessor 48 within monitor 14 to be processed.

In an embodiment, at step 1406, the signal may be transformed in any suitable manner. For example, a PPG signal may be transformed using a continuous wavelet transform as described above with respect to FIG. 3(c). In an embodiment, at step 1408, a scalogram may be generated based at least in part on the transformed signal. The scalogram of a PPG signal may be generated as described above with respect to FIGS. 3(a) and 3(b). For example, processor 412 or microprocessor 48 may perform the calculations associated with the continuous wavelet transform of the PPG signal and the derivation of the scalogram.

In an embodiment, at step 1410, at least one band (e.g., a band of scales) on the scalogram from step 1408 may be determined to not be of interest by processor 412 or microprocessor 48 in any suitable manner. For example, a band may be determined to not be of interest using, for example, any of the techniques described above with respect to FIGS. 5-13.

In an embodiment, at step 1412, if at least one band has been identified as being not of interest, that at least one band may be discriminated. For example, the at least one band may be marked or masked by processor 412 or microprocessor 48 such that any further processing of bands of interest, such as the pulse band and/or the breathing band in the context of the PPG signal, may ignore the marked bands (e.g., the ranges of scales within the scalogram that may be associated with the bands). Alternatively, the bands to be discriminated may be removed from the scalogram at step 1408 by replacing them with energy bands of a constant amplitude of zero or with energy bands derived dynamically according at least in part to, for example, features of the scalogram. Process 1400 may then advance to step 1414 and end. It will be understood that process 1400 may be modified in any suitable way and that the steps may be performed in any suitable order.

It will be understood that a particular band being examined for discrimination may be discriminated if either a single technique discussed above (or any other suitable technique) indicates that it is not a band of interest or if at least two or more of the techniques indicate that the band is not a band of interest. Each technique may further have associated weights.

The foregoing is merely illustrative of the principles of this disclosure and various modifications can be made by those skilled in the art without departing from the scope and spirit of the disclosure.

What is claimed is:

1. A method comprising:
generating a scalogram based at least in part on a continuous wavelet transform of a signal;
determining whether a first band of scales in the scalogram is negatively affected by a second band of scales; and
extracting the first band of scales in response to determining that the first band is negatively affected by the second band.

2. The method of claim 1 further comprising:
identifying the first band of scales from the scalogram; and
in response to determining that the first band of scales is negatively affected by the second band of scales, identifying a third band of scales from the scalogram.

3. The method of claim 1, wherein the determining is performed at least in part by a mod-max discriminator.

4. The method of claim 1, wherein the first band of scales is negatively affected by the second band of scales when the first band's energy amplitude is modulated by the second band.

5. The method of claim 1, wherein the determining further comprises:
computing energy of a source ridge candidate;
determining a threshold from the computed energy of the source ridge candidate;
computing energy of a profile ridge candidate; and
comparing the computed energy of the profile ridge candidate to the threshold.

6. The method of claim 1, wherein the signal is a photoplethysmograph signal.

7. The method of claim 1, wherein the extracting removes the first band of scales from the scalogram.

8. The method of claim 1 further comprising replacing the first band of scales with energy bands of constant amplitude.

9. The method of claim 1 further comprising replacing the first band of scales with energy bands derived dynamically according at least in part to features of the scalogram.

10. A system comprising control circuitry configured to:
generate a scalogram based at least in part on a continuous wavelet transform of a signal;
determine whether a first band of scales in the scalogram is negatively affected by a second band of scales; and
extract the first band of scales in response to determining that the first band is negatively affected by the second band.

11. The system of claim 10, wherein the control circuitry is further configured to:
identify the first band of scales from the scalogram; and
in response to determining that the first band of scales is negatively affected by the second band of scales, identify a third band of scales from the scalogram.

12. The system of claim 10, wherein the determining is performed at least in part by a mod-max discriminator.

13. The system of claim 10, wherein the first band of scales is negatively affected by the second band of scales when the first band's energy amplitude is modulated by the second band.

14. The system of claim 10, wherein the control circuitry is further configured to:
compute energy of a source ridge candidate;
determine a threshold from the computed energy of the source ridge candidate;
compute energy of a profile ridge candidate; and
compare the computed energy of the profile ridge candidate to the threshold.

15. The system of claim 10, wherein the signal is a photoplethysmograph signal.

16. The system of claim 10, wherein the control circuitry is further configured to remove the first band of scales from the scalogram.

17. The system of claim 10, wherein the control circuitry is further configured to replace the first band of scales with energy bands of constant amplitude.

18. The system of claim 10, wherein the control circuitry is further configured to replace the first band of scales with energy bands derived dynamically according at least in part to features of the scalogram.

19. A non-transitory computer-readable medium having computer program instructions stored thereon, if executed by a machine are capable of:
   generating a scalogram based at least in part on a continuous wavelet transform of a signal;
   determining whether a first band of scales in the scalogram is negatively affected by a second band of scales; and
   extracting the first band of scales in response to determining that the first band is negatively affected by the second band.

20. The non-transitory computer-readable medium of claim 19, wherein the signal comprises a photoplethysmograph signal, and wherein the computer readable instructions are executed at least in part by a pulse oximeter.

* * * * *